(12) United States Patent
Cronin

(10) Patent No.: US 12,064,740 B2
(45) Date of Patent: Aug. 20, 2024

(54) NETWORKED REACTION SYSTEMS

(71) Applicant: Chemify Limited, Glasgow (GB)

(72) Inventor: Leroy Cronin, Glasgow (GB)

(73) Assignee: Chemify Limited, Glasgow (GB)

( * ) Notice: Subject to any disclaimer, the term of this patent is extended or adjusted under 35 U.S.C. 154(b) by 986 days.

(21) Appl. No.: 16/978,591

(22) PCT Filed: Mar. 6, 2019

(86) PCT No.: PCT/EP2019/055609
§ 371 (c)(1),
(2) Date: Sep. 4, 2020

(87) PCT Pub. No.: WO2019/170772
PCT Pub. Date: Sep. 12, 2019

(65) Prior Publication Data
US 2021/0031162 A1    Feb. 4, 2021

(30) Foreign Application Priority Data

Mar. 6, 2018 (GB) ...................................... 1803549

(51) Int. Cl.
*B01J 19/00* (2006.01)
*G06Q 50/00* (2024.01)

(52) U.S. Cl.
CPC ......... *B01J 19/0033* (2013.01); *B01J 19/004* (2013.01); *G06Q 50/01* (2013.01)

(58) Field of Classification Search
CPC .................. B01J 19/0033; B01J 19/004; B01J 2219/00585; B01J 2219/0059;
(Continued)

(56) References Cited

U.S. PATENT DOCUMENTS 6,044,212 A * 3/2000 Flavin ................. B01J 19/0046
703/11
2003/0012700 A1   1/2003 Carnahan
(Continued)

FOREIGN PATENT DOCUMENTS

GB        2372506       8/2002
WO    2013/175240      11/2013

OTHER PUBLICATIONS

Bennet & Pence (2011) "Managing Laboratory Data Using Cloud Computing as an Organizational Tool", Journal of Chemical Education 88:761-763.
(Continued)

*Primary Examiner* — Jill A Warden
*Assistant Examiner* — John McGuirk
(74) *Attorney, Agent, or Firm* — Rudy J. Ng; Bozicevic, Field & Francis LLP

(57) ABSTRACT

The present invention provides a system for performing reactions, where the system comprises a plurality of synthesisers that are in communication via a communal reporting platform. A synthesiser is programmed for the automated synthesis of one or more chemical or biological reactions, and the synthesiser comprises a reaction vessel which is supplied by a reagent delivery system, an analytical system for analysing a reaction, and a controller for managing the reagent delivery system and the analytical system, and for communication with the reporting platform. Also provided are methods for performing a plurality or reactions using the system.

19 Claims, 25 Drawing Sheets

(58) Field of Classification Search
CPC .... B01J 2219/00689; B01J 2219/00695; B01J 2219/00698; B01J 2219/007; B01J 2219/00702; B01J 2219/0072; B01J 2219/00745; B01J 2219/0075; B01J 19/0046; G06Q 50/01; G16C 20/10
See application file for complete search history.

(56) References Cited

U.S. PATENT DOCUMENTS

| | | | |
|---|---|---|---|
| 2005/0082351 A1* | 4/2005 | Pinchot | B01J 19/0093 228/215 |
| 2008/0286174 A1 | 11/2008 | Diamond et al. | |
| 2011/0202177 A1 | 8/2011 | Elizarov et al. | |
| 2015/0291927 A1 | 10/2015 | Liu | |
| 2016/0288081 A1 | 10/2016 | Moonen et al. | |
| 2018/0010058 A1 | 1/2018 | Kirchmann et al. | |

OTHER PUBLICATIONS

Caramelli et al., (2018) "Networking Chemical Robots for Reaction Multitasking", Nature Commun. 9(1), 3406:1-10.
Prabhu et al., (2017) "The Dawn of Unmanned Analytical Laboratories", Trends Anal. Chem. 88, 41-52.
Search Report for GB 1803549.3 dated Sep. 28, 2018, 4 pages.
Search Report and Opinion for PCT/EP2019/055609 dated May 3, 2019, 16 pages.
Baker, M. & Penny D. "Is there a Reproducibility Crisis?", Nature vol. 533, 452-454k, May 26, 2016.
Blagojevic, S. M., et al., "Malonic Acid Concentration as a Control Parameter in the Kinetic Analysis of the Belousov-Zhabotinsky Reaction under Batch Conditions", Physical Chemistry Chemical Physics vol. 10, 6658 (2008).
Epstein, I. R. & Showalter, K., "Nonlinear Chemical Dynamics: Oscillations, Patterns and Chaos", J. Phys. Chem. vol. 100, 13132-13147, Jan. 17, 1996.
Gung, B.W. & Taylor, R. T. "Paralell Combinatorial Syntehesis of Azo Dyes", Journal of Chemical Education, vol. 81, 144-148, Nov. 11, 2004.
Ingham, R. J et al., "A Systems Approach Towards an Intelligent and Self-Controlling Platform for Integrated Continuous Reaction Sequences", Angew. Chemie—Int. Ed., vol. 54, 144-148 (2015).
Kitson, P. J., Glatzel, S., Cronin, L., "The Digital Code Driven Autonomous Synthesis of Ibuprogen Automated in a 3D—Printer-Based Robot" Beilstein Journal of Organic Chemistry, vol. 12, 2776-2783, Dec. 19, 2016.
Li, J. et al., "Synthesis of Many Different Types of Organic Small Molecules Using One Automated Process", Science vol. 347, 1221-1226, Mar. 13, 2015.
Makki, R., Muuzuri, A. P. & Perez-Mercader, "Periodic Perturbation of Chemical Oscillators: Entrainment and Induced Synchronization", J. Chem.—A Eur. J. vol. 20, 14213-14217 (2014).
Perkel, J. M., "The Internet of Things Comes to the Lab", Nature, vol. 542, 125-126, Feb. 2, 2017.
Pronk, S. et al., "GROMACS 4.5: A High-Throughput and Highly Parallel Open Source Molecular Simulation Toolkit" vol. 29, No. 7, 845-854, Jan. 29, 2013.
Schrope, M., "Solving Tough Problems with Games" Proc. Natl. Acad. Sci., vol. 110, 7104-7106 Apr. 30, 2013.
Skilton, R. A. et al., "Remote-Controlled Experiments with Cloud Chemistry", Nature Chemistry, vol. 7, Jan. 1-5, 2015.
Sorensen, J. J. W. H. et al., "Exploring the Quantum Speed Limit With Computer Games", Nature, vol. 532, 210-213 Apr. 14, 2016.
Symes, M. D. et al., "Integrated 3D-Printed Reactionware for Chemical Synthesis and Analysis" Nature Chemistry vol. 4, 349-354, May 2012.
Machida et al., (2010) "Development and Application of a Solution-Phase Automated Synthesizer, 'ChemKonzert" Chem Pharm Bull. 58(1), 87-93.

* cited by examiner

Figure 5

NETWORKED REACTION SYSTEMS

RELATED APPLICATION

The present application claims the benefit of and priority to GB 1803549.3, filed on 6 Mar. 2018 (6 Mar. 2018), the contents of which are hereby incorporated by reference in their entirety.

FIELD OF THE INVENTION

The present invention provides a system for use in automated chemical or biological synthesis, for example for the validation of syntheses, assessing reproducibility using a chemical-digital-code, and discovery of new molecules and methods. Also provided are methods for preparing chemical or biological products by cooperative methods utilising the system of the invention.

BACKGROUND

The digitisation of everyday life through the computer and internet revolution has led to systems that allow error-correction, distributed 'multi-core' working, and gamification of task-based work (see, for example Perkel; Pronk et al.; Schrope; and Sorensen). Thus digitization has led to an explosion in cooperativity driven by common standards and protocols which means that tasks centrally managed can be distributed over many sites, yet this approach has yet to impact the field of chemistry (see Sorensen; Skilton, R. A. et al.).

However, the automation of chemical reactions has been an expanding field in the last decade including flow chemistry, peptide and nucleic acid synthesis (Machida et al.). These robotic systems are specialised and expensive ($50-500K) so the adoption of such automation in chemistry has been limited. This is because using robots to do chemistry is hard due to the bespoke nature of many chemical operations reactions resulting from a lack of standards (Ingham et al.; Li et al.).

WO 2013/175240 describes an automated procedure for exploring a chemical space. Here, a flow system is used to generate a range of products from a series of chemical and physical and inputs. A genetic algorithm controls the operation of the system by selecting future chemical and physical inputs based on the analysis of the products produced, and their ranking against a set fitness function, which is a desirable property to be obtained in the exploration of the chemical space. The flow system operates in isolation and a satisfactory exploration of the available chemical space is achieved only by the serial operation of the flow system.

There is a need therefore for systems and processes to explore chemical and biological reaction spaces in a timely and efficient manner.

SUMMARY OF THE INVENTION

The present invention provides a cooperative system for use in automated chemical or biological synthesis, for example for the discovery of new chemical and biological entities.

In a first aspect of the invention there is provided a system comprising a plurality of synthesisers that are in communication via a communal reporting platform.

A synthesiser is programmed for the automated synthesis of one or more chemical or biological reactions, and the synthesiser comprises a reaction vessel which is supplied by a reagent delivery system, an analytical system for analysing a reaction, and a controller for managing the reagent delivery system and the analytical system, and for communication with the reporting platform, which also includes feedback control.

A synthesiser is an automated reaction system for use in chemical and biological synthesis, with the synthesiser comprising a reaction vessel for chemical or biological reactions and an analytical system for analysis of a reaction mixture or components from the reaction mixture, including a reaction product. The synthesiser may be provided with a purification system for the at least partial purification of a reaction mixture.

Each synthesiser is provided with a controller, which is responsible for the operation of the synthesiser, and it coordinates the reagent delivery system, the reaction of those reagents within the reaction vessel and the analysis of the reaction products.

The automated synthesiser may be referred to as a chemical robot, owing to its autonomous ability to select reagents for use in the preparation of reaction products, and its ability to analyse those products and provide a report of the synthesis. The system also has the ability to select future reactions for performance, through suitable programming of the synthesiser or the reporting platform, with which the synthesiser is in communication.

The reporting platform may be a server that is accessible to all synthesisers in the system. The synthesisers are able to report to the platform and receive information from the platform. In this way, the system allows individual synthesisers to cooperate within the greater system by providing a mechanism to share synthesis information between all participants. In this way, a reaction space may be explored rapidly and without significant overlap or repetition in the work of the synthesisers.

In another use of the system, individual synthesisers within the system may be suitably programmed to repeat the work of one or more other synthesisers, thereby to provide an independent validation of the earlier work. Thus the system uses cooperativity to verify reaction results, thereby providing an assurance of a reaction outcome and its association with a particular set of reaction conditions.

The reporting platform receives information from a synthesiser and combines that information with information received from all other synthesisers in the system to give an overview of the results from all of the synthetic processes undertaken by the synthesisers. Each synthesiser is able to access the combined information forming the overview. A synthesiser having this information is then able to select a future synthesis method having knowledge of the synthesis methods performed by other synthesisers in the system.

Each synthesiser is capable of reporting as least two types of information to the reporting platform. The first is information regarding an intended synthesis to be undertaken by the synthesiser. The second is information regarding the results of a synthesis undertaken by the synthesiser.

The reporting platform may be an open-use platform for posting information to and for receiving information from. The reporting platform may be an open-use platform having private or public reporting functions. Thus, details of reactions, including planned reactions and reaction results, may be shared only with approved users, such as approved synthesisers, in a private group, or the details may be made publically available to all.

The reporting platform may be a platform where only approved users have access to reported reaction details.

The present invention also provides a method of performing a plurality or reactions, the method comprising the steps of:
  (i) providing a system according to the first aspect of the invention, where the system comprises a plurality of synthesisers that are in communication via a communal reporting platform;
  (ii) permitting each synthesiser to select a reaction for performance, and allowing each synthesiser to post its intended reaction to the reporting platform;
  (iii) allowing each synthesiser to perform the reaction and to post a reaction result to the reporting platform;
  (iv) allowing each synthesiser to observe the combined reaction results posted on the reporting platform; and
  (v) permitting each synthesiser to select a future reaction for performance, where that future reaction optionally differs from the reactions previously reported by all synthesisers to the reporting platform.

Preferably, each reaction undertaken by a synthesiser is unique, and has not previously been undertaken by a synthesiser in the system.

Step (vi), which follows step (v), comprises each synthesiser to post its intended reaction to the reporting platform, and then performing the selected future reaction. Following the completion of the reaction, step (iii) may be repeated optionally also together with steps (iv), (v) and (vi). These steps may be repeated as required to allow the system to undertake the desired number of reactions, such as might be needed to occupy the available chemical space.

A reaction may be unique if, for example, it differs in one or more of an identity of a reagent, catalyst or solvent, or differs in one or more of an amount of a reagent, catalyst or solvent or in a reaction condition, such as temperature or light exposure.

The products of each reaction may be the same or different. Where they are the same, the system may be use to explore the reaction conditions for the preparation of that product.

These and other aspects and embodiments are described in further detail herein.

The synthesisers receive the reactions parameters from the cloud in order to explore a chemical space in an optimized way, when the reactions are done the analysis results are returned and shared trough the cloud.

Figure 2:
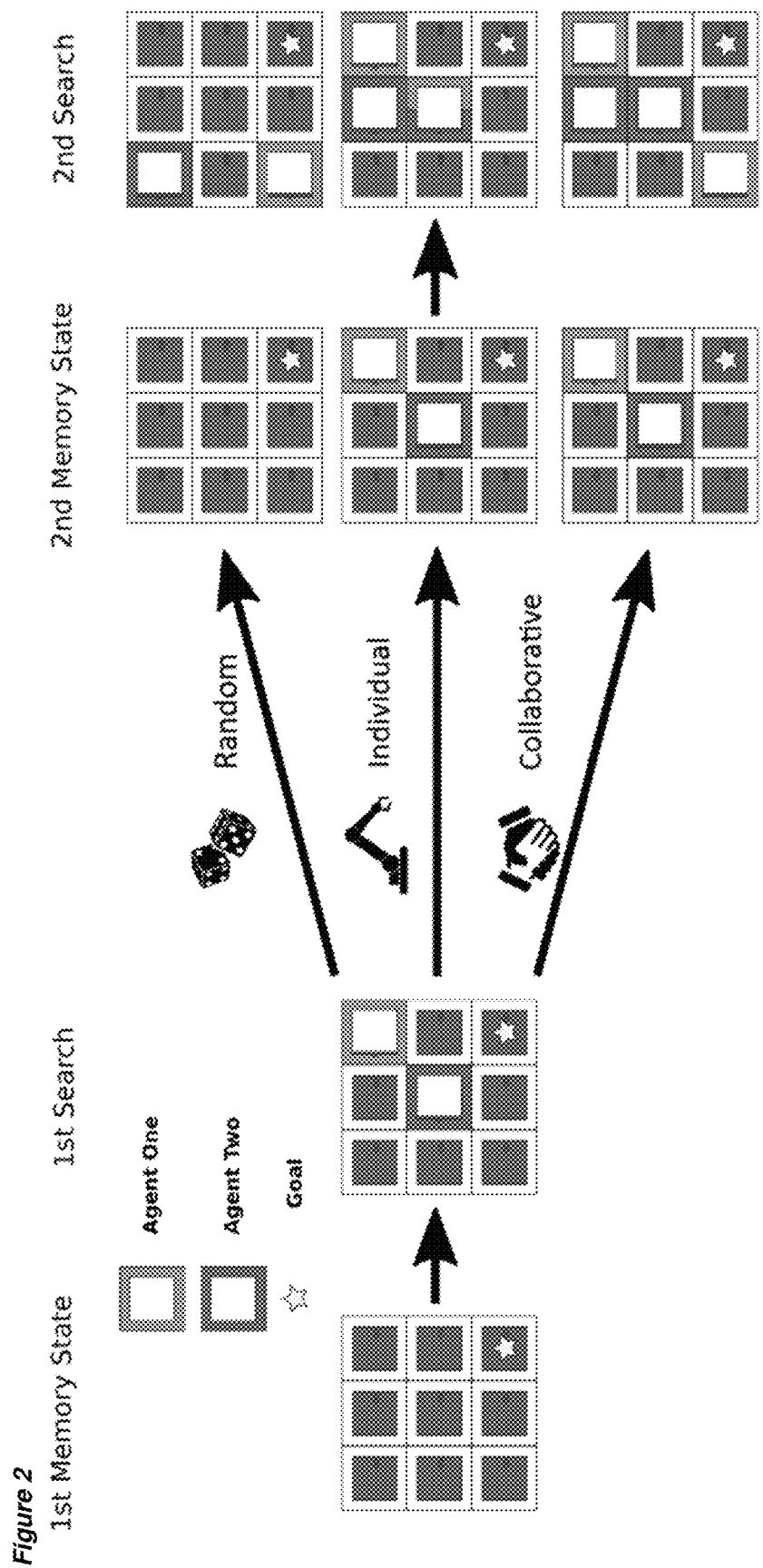
Figure 2:
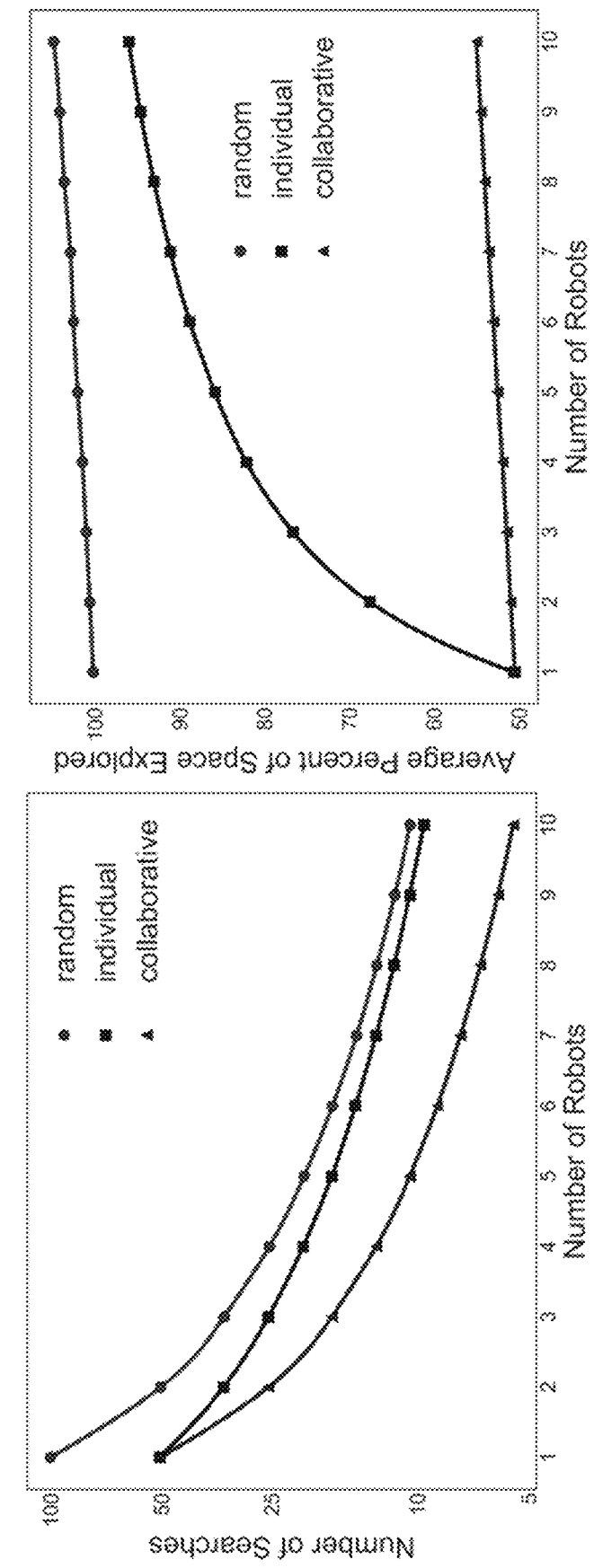

FIG. 2 is (top) a schematic of a scheme showing the simulated search of a reaction space with three different search strategies, random, individual and collaborative; and (bottom) the plot on the left shows the average number of searches needed under each strategy as a function of the number of robots, and the plot on the right shows the search efficiency in terms of the percentage of the chemical space that had to be explored.

Figure 3:
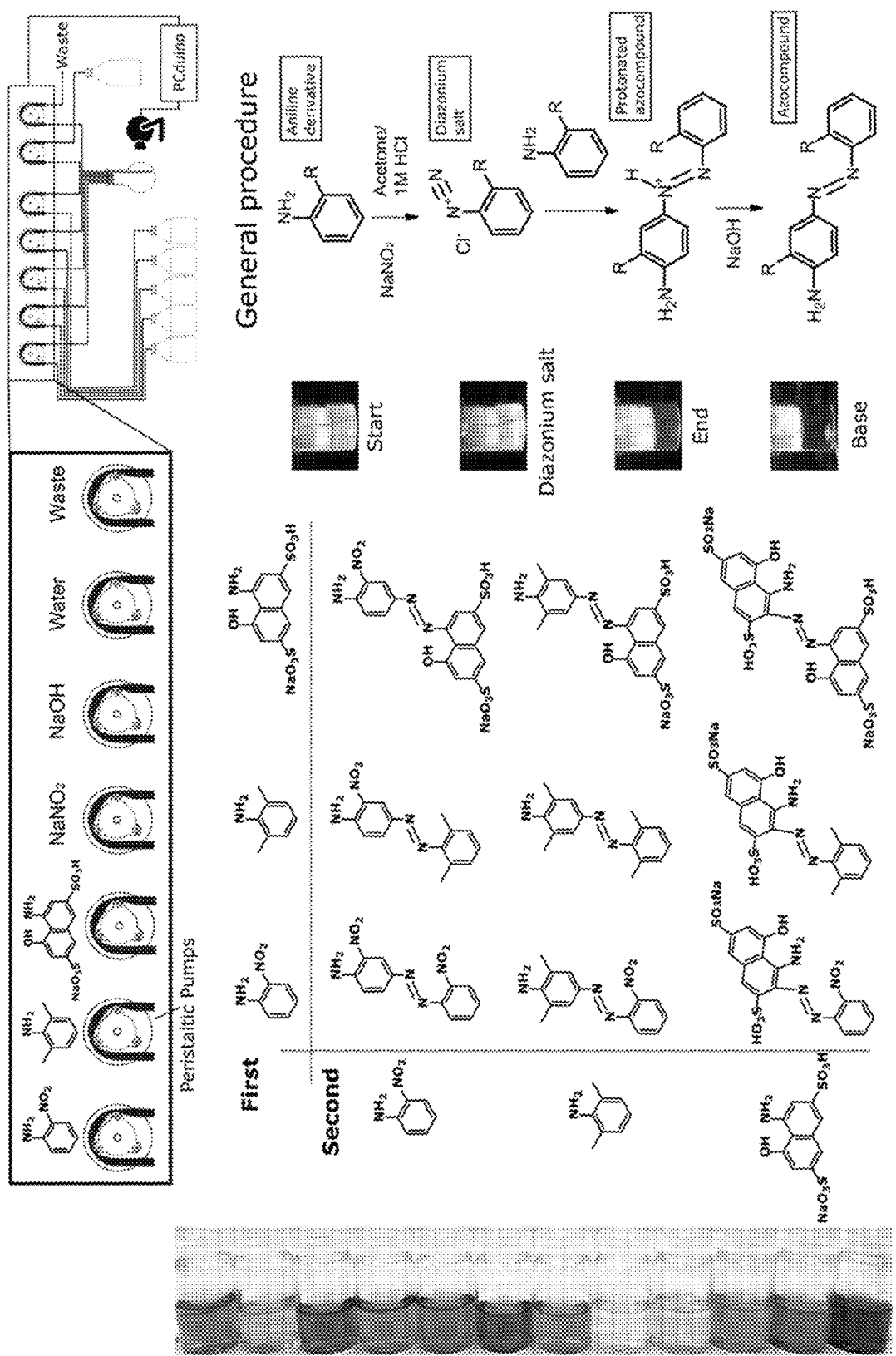

FIG. 3 is (top) a schematic of a synthesiser according to an embodiment of the invention, showing a reaction vessel that is supplied by reagents that are pumped into the vessel. A video camera is also provided as part of an analytical system of the synthesiser; (centre, left) a summary of an azo-coupling reaction space available from first and second reagents used in an exemplary method according to an embodiment of the invention; (centre, right) a schematic of the azo-coupling reaction, showing the change in colour over time; and (bottom) an image of the colour profile available for the products in the azo-coupling reaction space.

Figure 4:
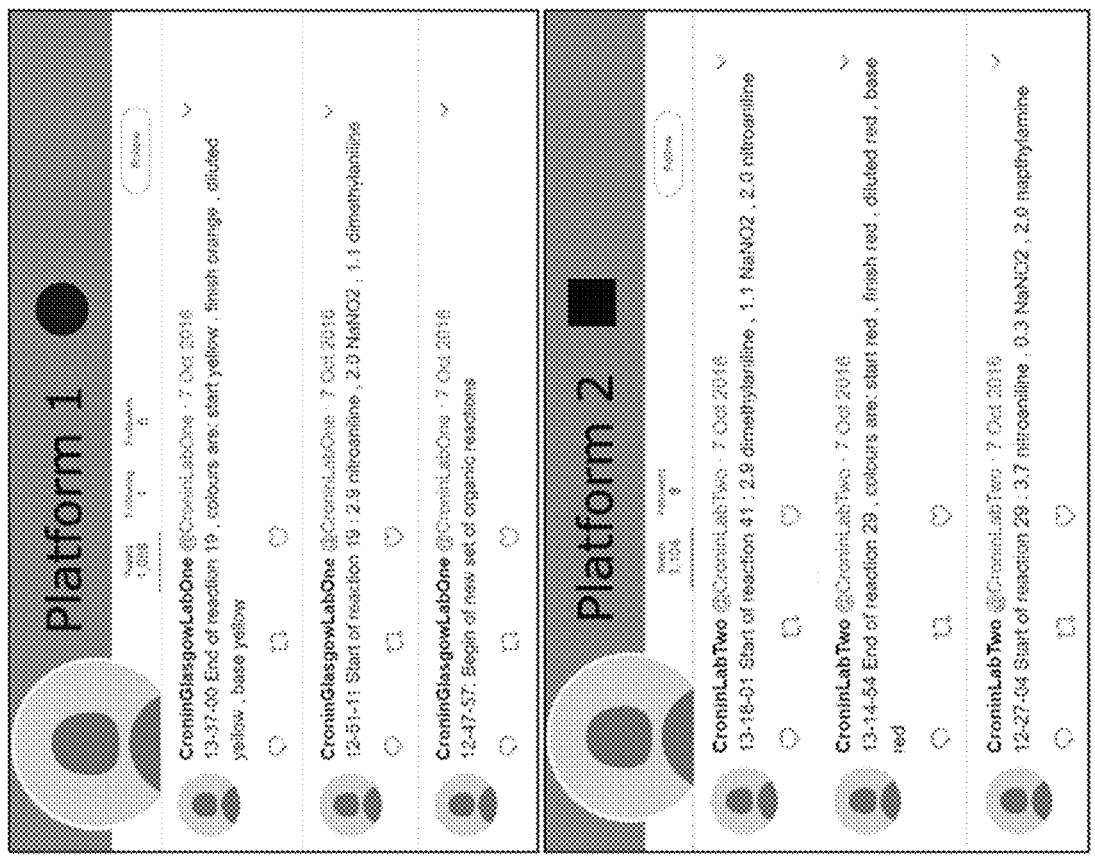
Figure 4:
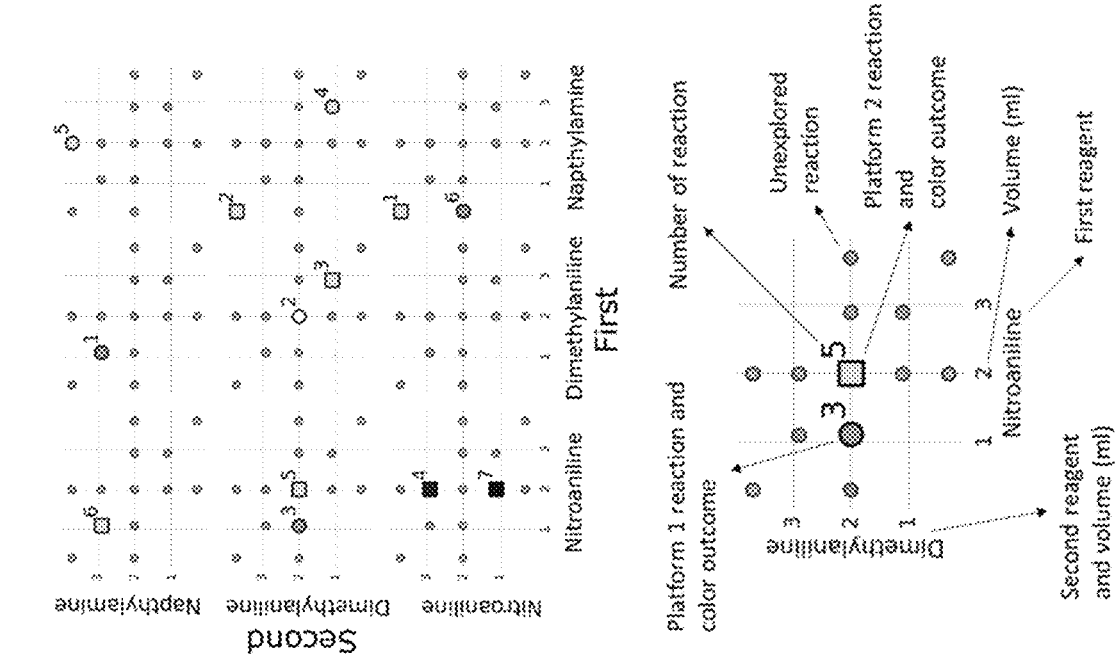

FIG. 4 shows (left) an example of the azo-coupling reaction space explored by first and second synthesisers, where a circle is a product of a first synthesiser, and a square is a product of a second synthesiser; and (right) the reaction details, including intended reaction and reaction results, that were posted to Twitter, acting as a reporting platform in an embodiment of the invention.

Figure 5:
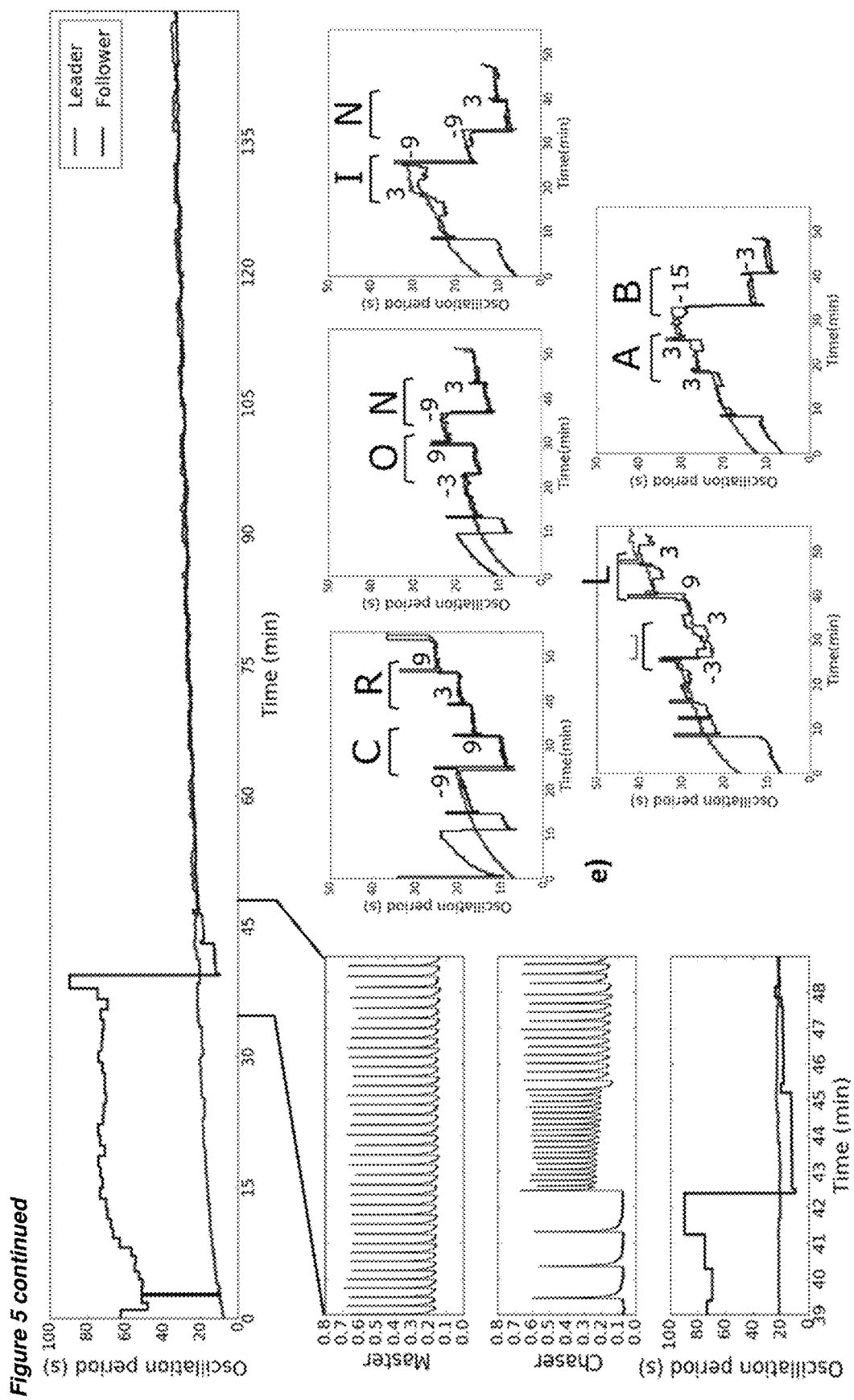

FIG. 5 shows BZ reaction synchronization achieved by two units acting as Leader and Follower. In the bottom an example of encoding procedure for the word "cron". On the right real data of encoding/decoding of "cronin lab".

Figure 6:
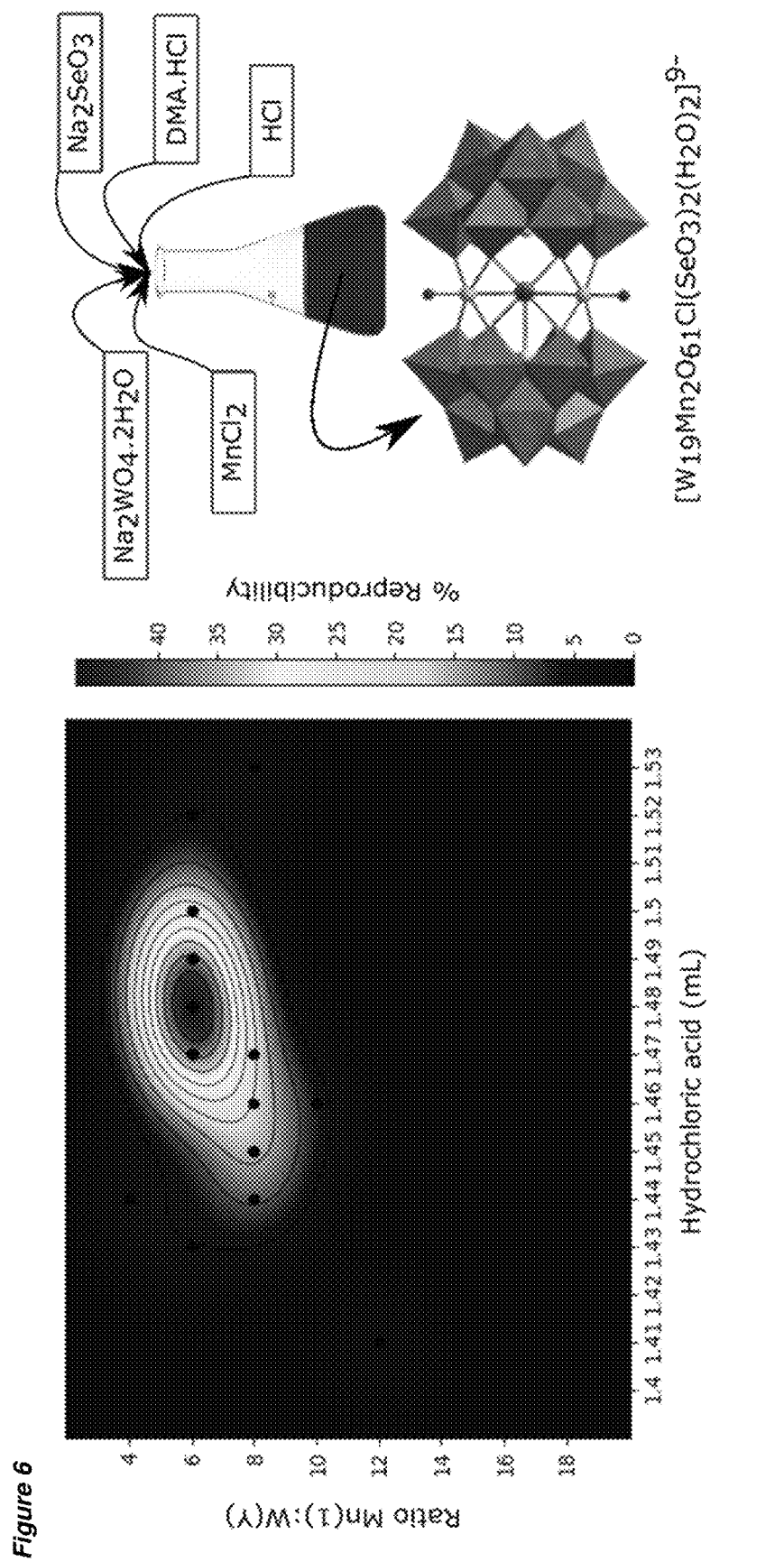
Figure 6:
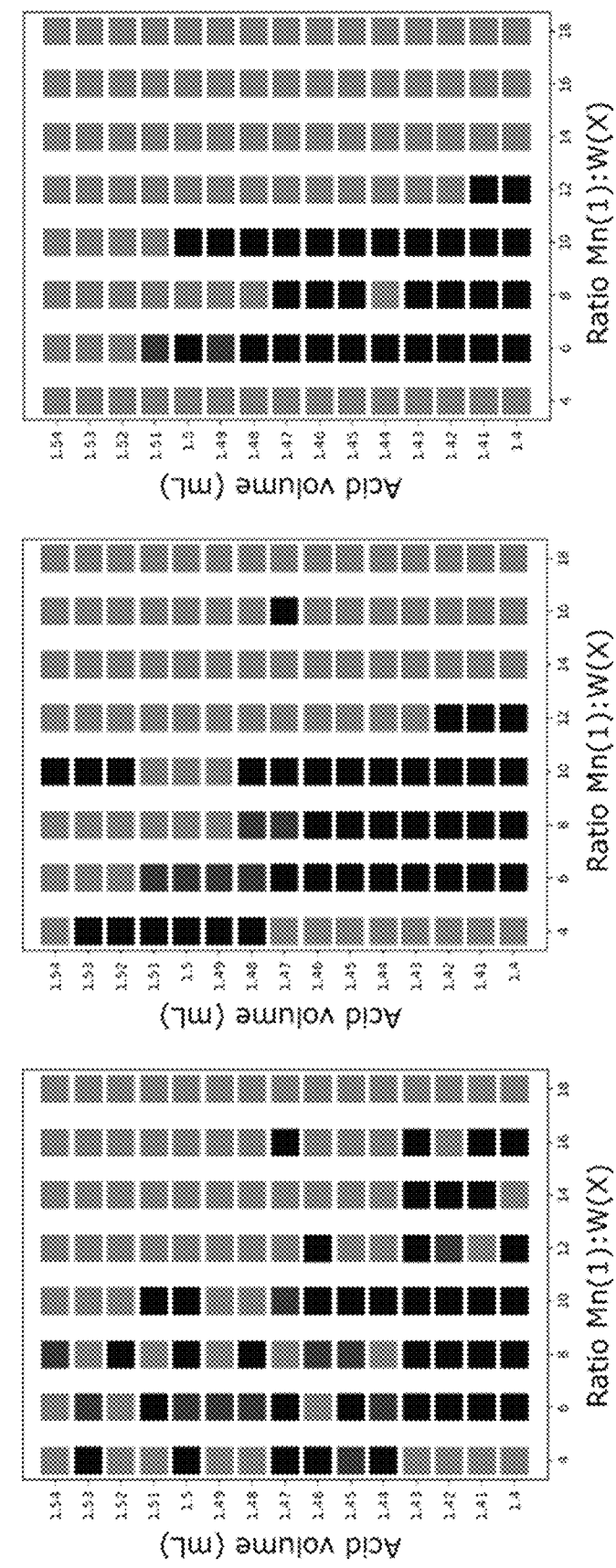

FIG. 6 shows (bottom) three automated grid search results for a polyoxometalate reaction space (where red in the grid indicates a crystal product, grey indicates a precipitate products, and black indicates no crystals); (top, left) is the heat map of % reproducibility for each reaction that produced crystals at least once; and (top, right) a schematic of a one-pot synthesis of the $W_{19}Mn_2Se_2$ polyoxometalate cluster with the accompanying structure shown.

Figure 7:
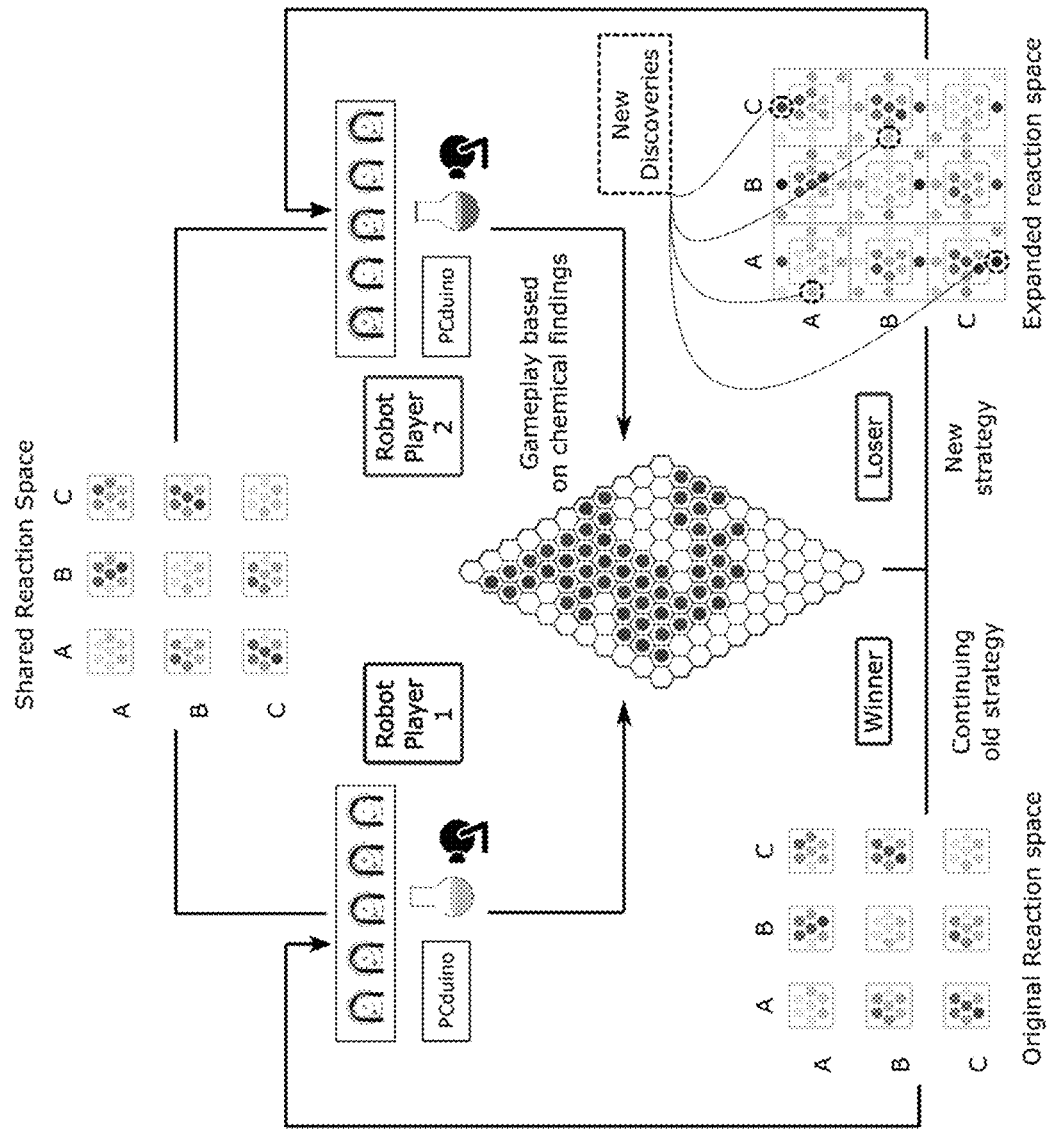

FIG. 7 is a schematic of a reaction game played according to an embodiment of a method of the invention, where Player 1 plays against Player 2 in a series of Hex games. Strategies for play change once the initial game winner and loser have emerged.

Figure 8:
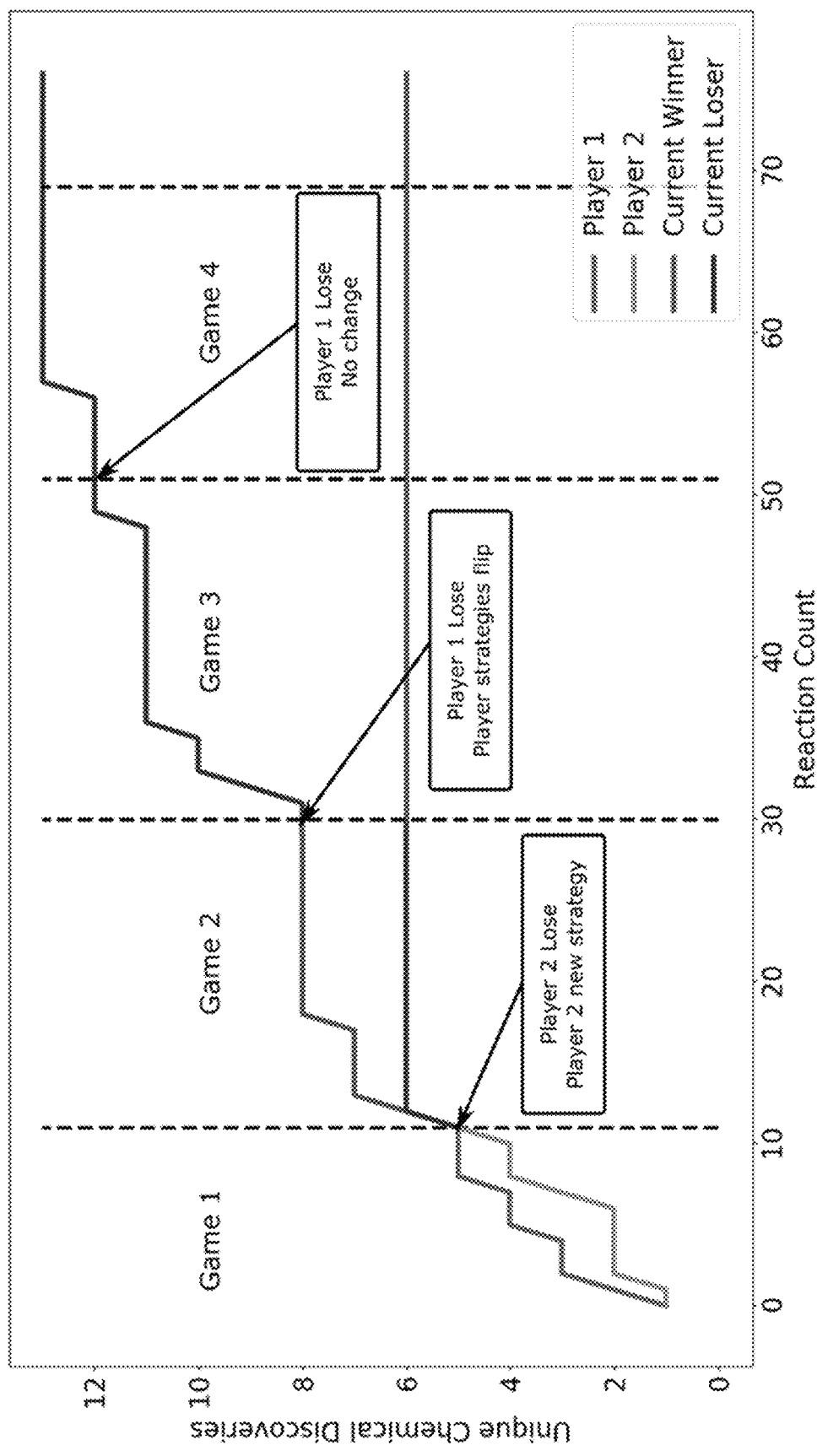

FIG. 8 shows the number of unique product discoveries over time (as measured by reaction count) in a four Hex game sequence between two automated synthesisers, where player 1 and 2 are shown, who are subsequently designated as winners and losers as each Hex game sequence is complete.

Figure 9:
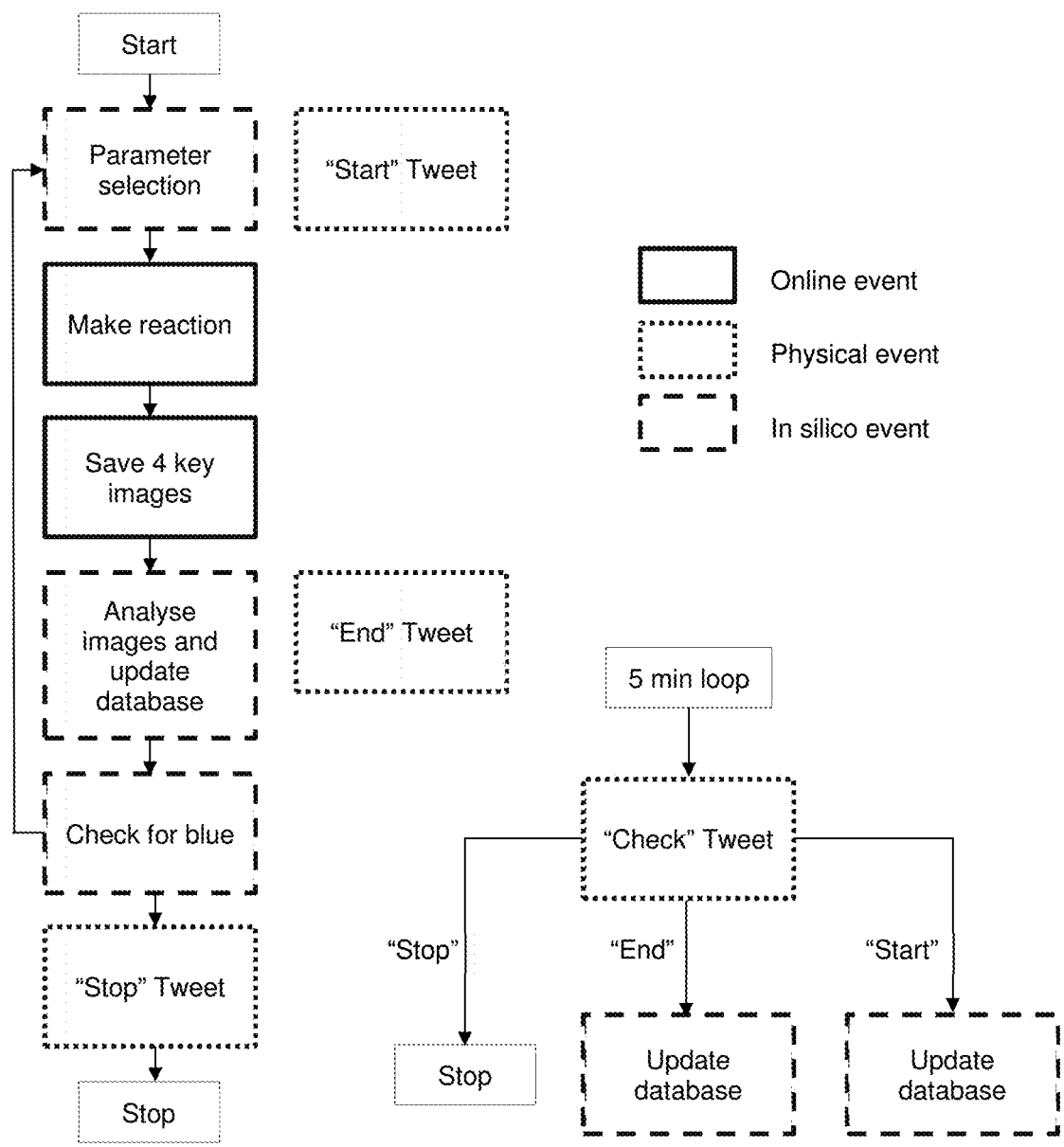

FIG. 9 is a schematic flow diagram for the collaborative algorithm run by two identical and cooperating platforms. It had a main thread (left) that managed the reaction making, data saving/analyzing and result sharing. The second thread (right) checked every 5 minutes the other board results and updates the database.

Figure 10:
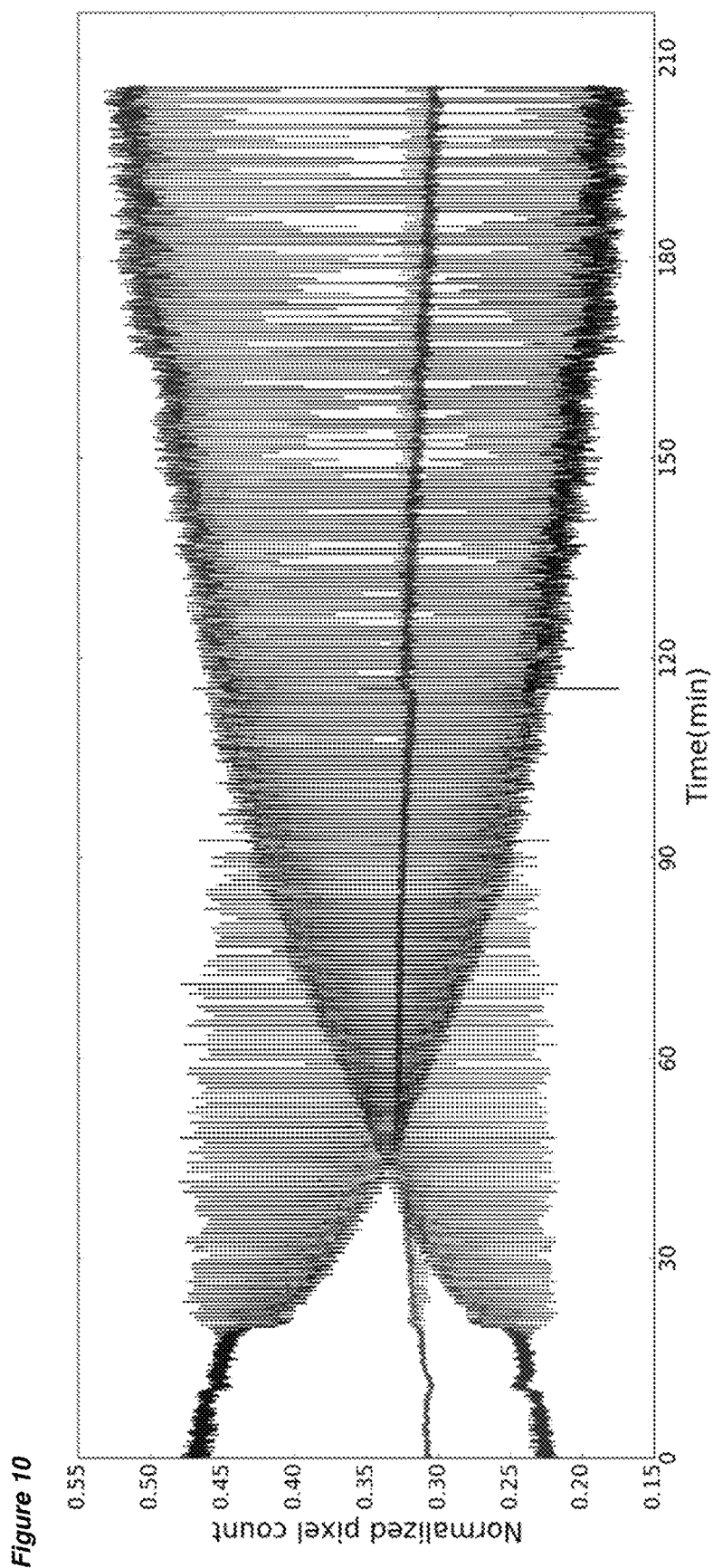
Figure 10:
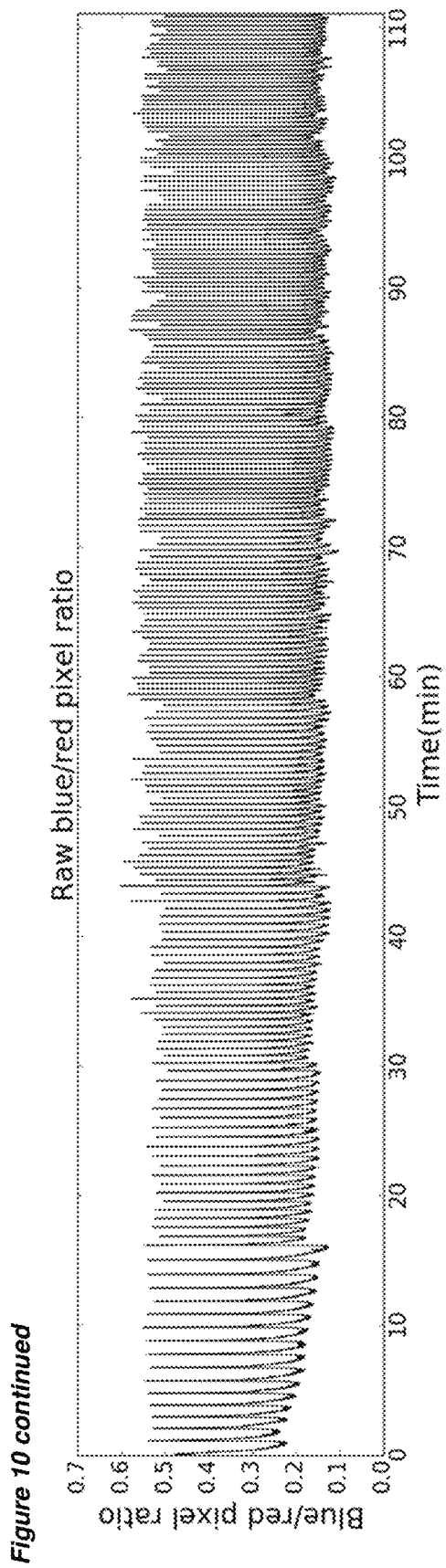
Figure 10:
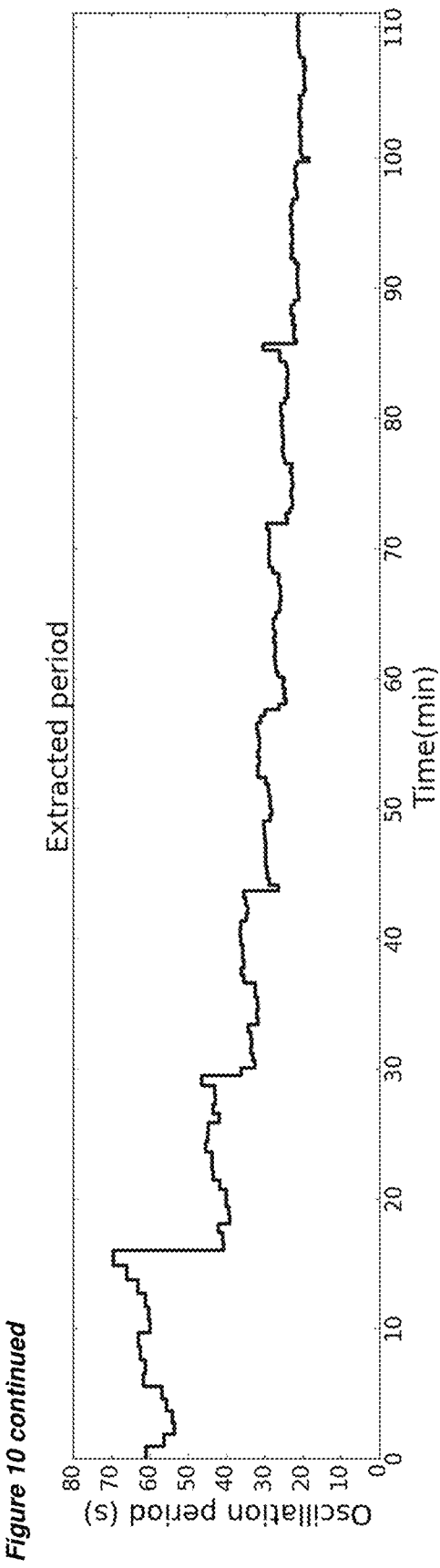

FIG. 10 shows (top) the normalized blue and red pixel count over time (min) for a BZ oscillation reaction. The average green count is also shown over the same time, where the green pixels are approximately constant over the time course of the reaction. The oscillations start at around 20 minutes. At the reaction end at 200 minutes, there were around 540 oscillations; (middle) the change in the relative blue/red pixel ratio over time (min) for a BZ oscillation reaction; and (bottom) the change in the oscillation ratio (s) over the same time period.

Figure 11:
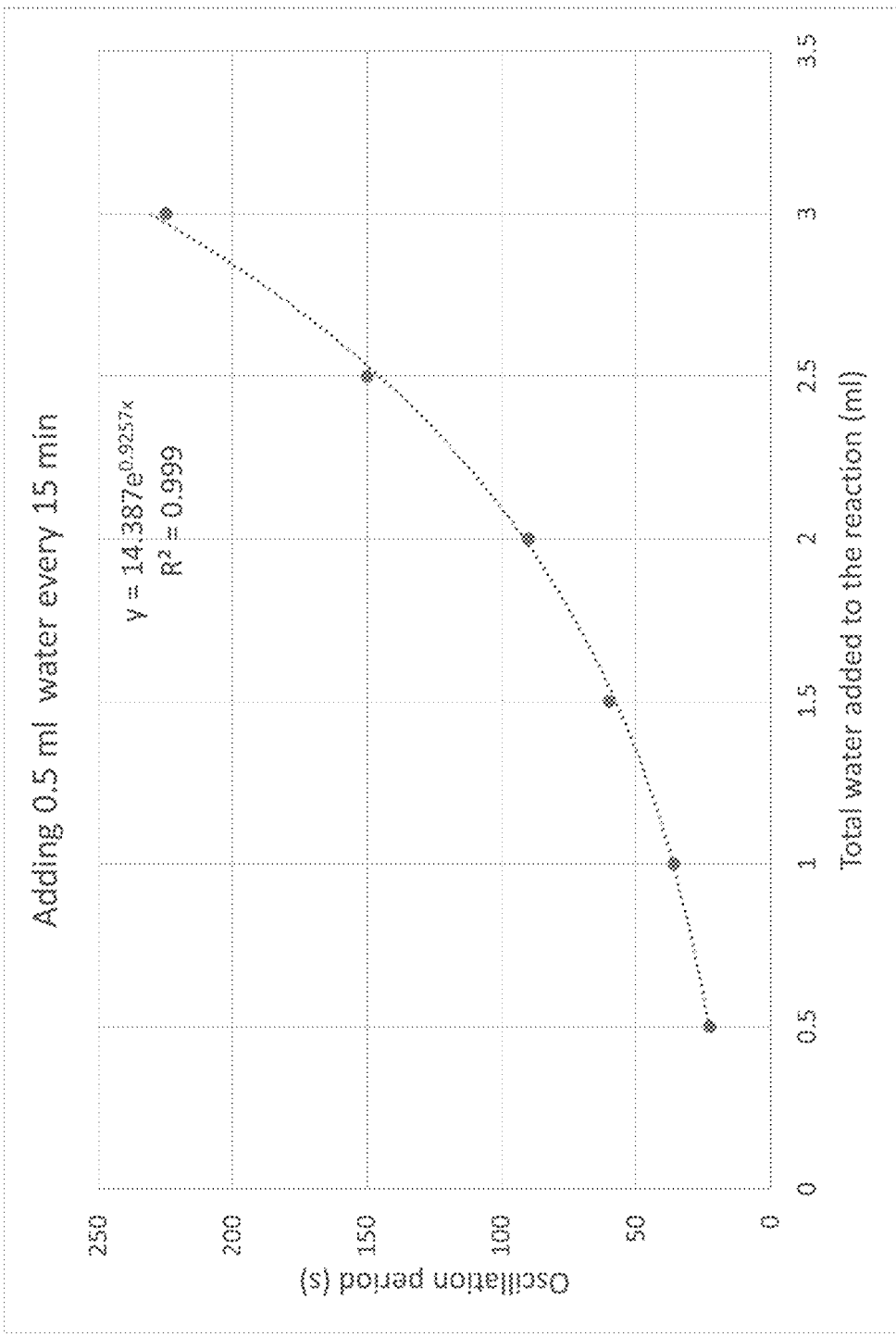
Figure 11:
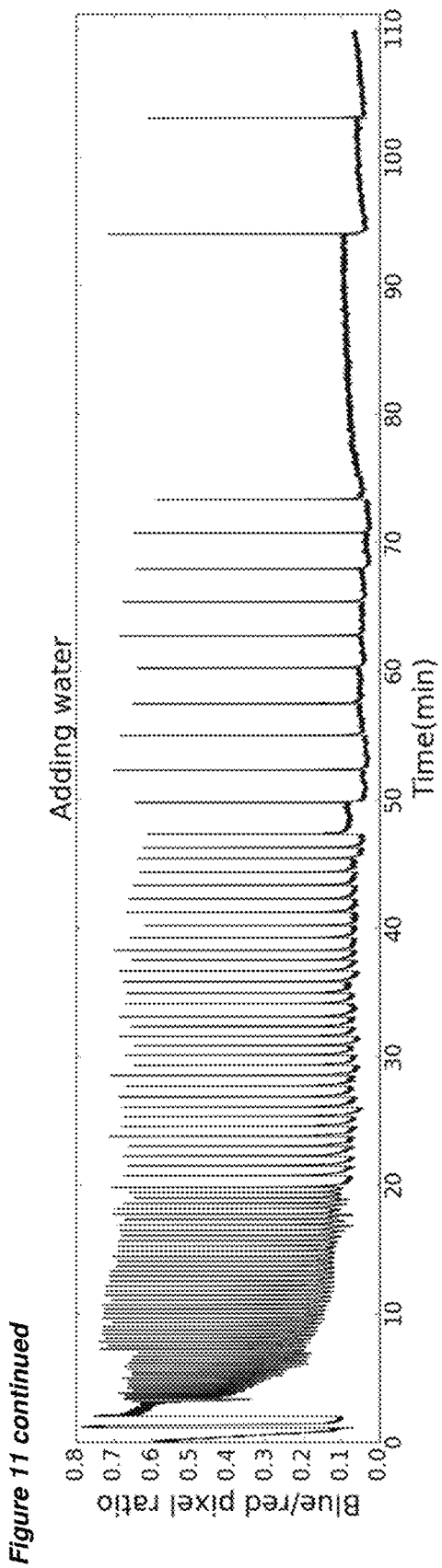
Figure 11:
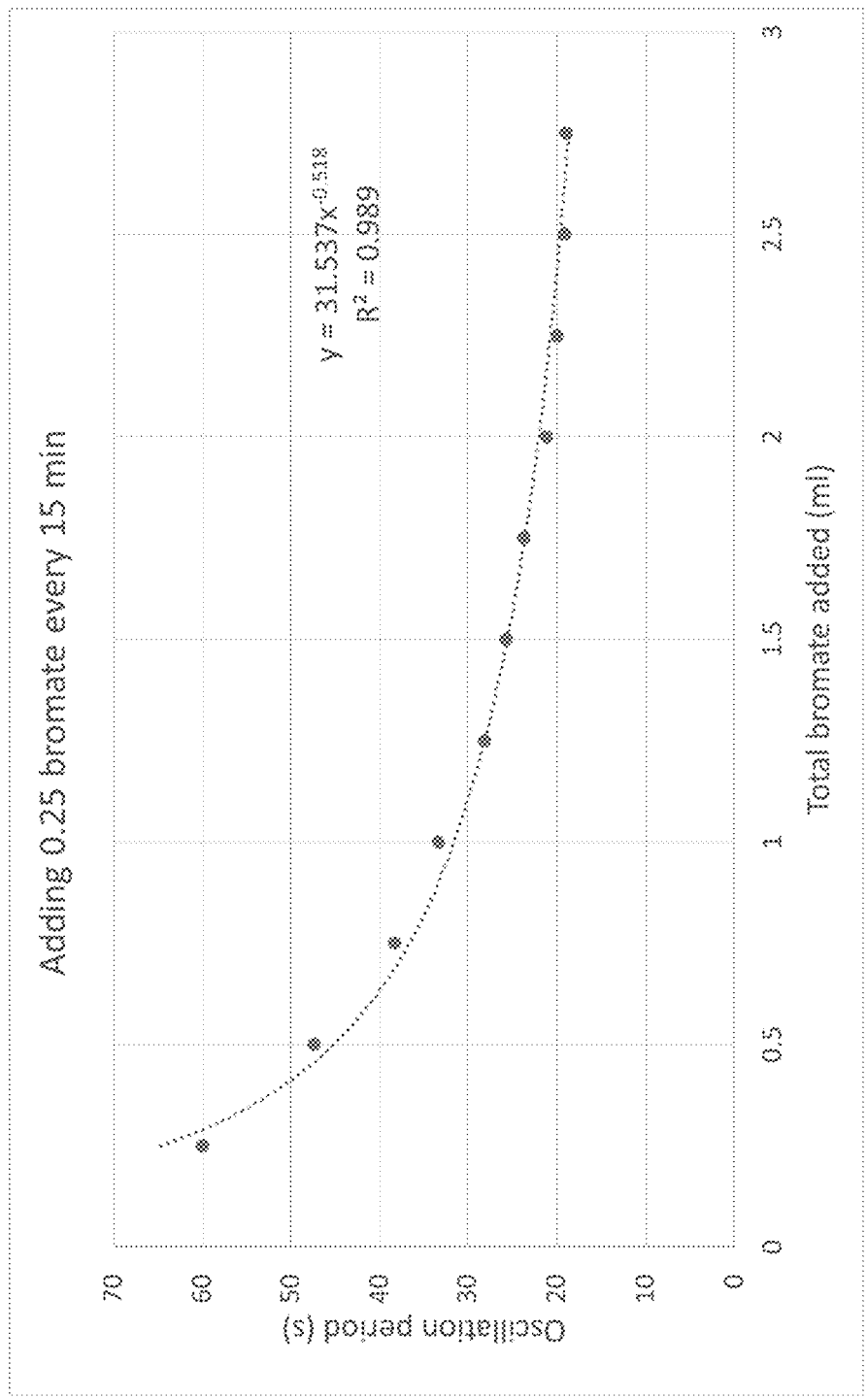
Figure 11:
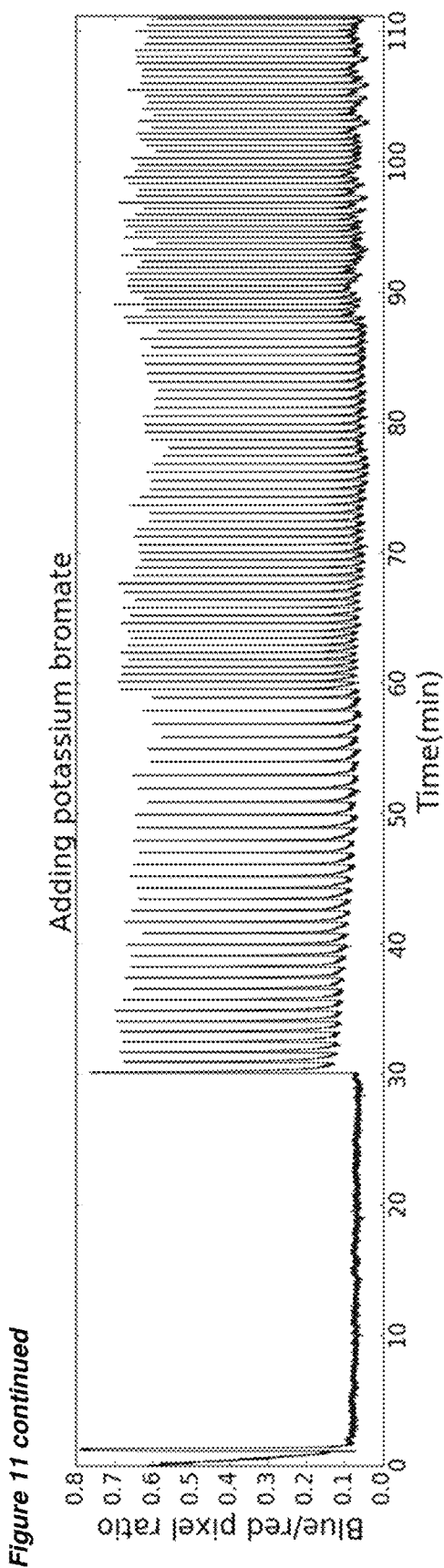

FIG. 11 shows (top) the change in oscillation period (s) for a BZ oscillation reaction in response to the total amount of water added to the reaction (mL); and (second from bottom) the change in oscillation period (s) for a BZ for oscillation reaction in response to the total amount of bromate added to the reaction (mL of 0.25 M solution). Also shown is the change in the relative blue/red pixel ratio over time (min) for the same reactions, with the addition of water (second from top) and bromate (bottom).

Figure 12:
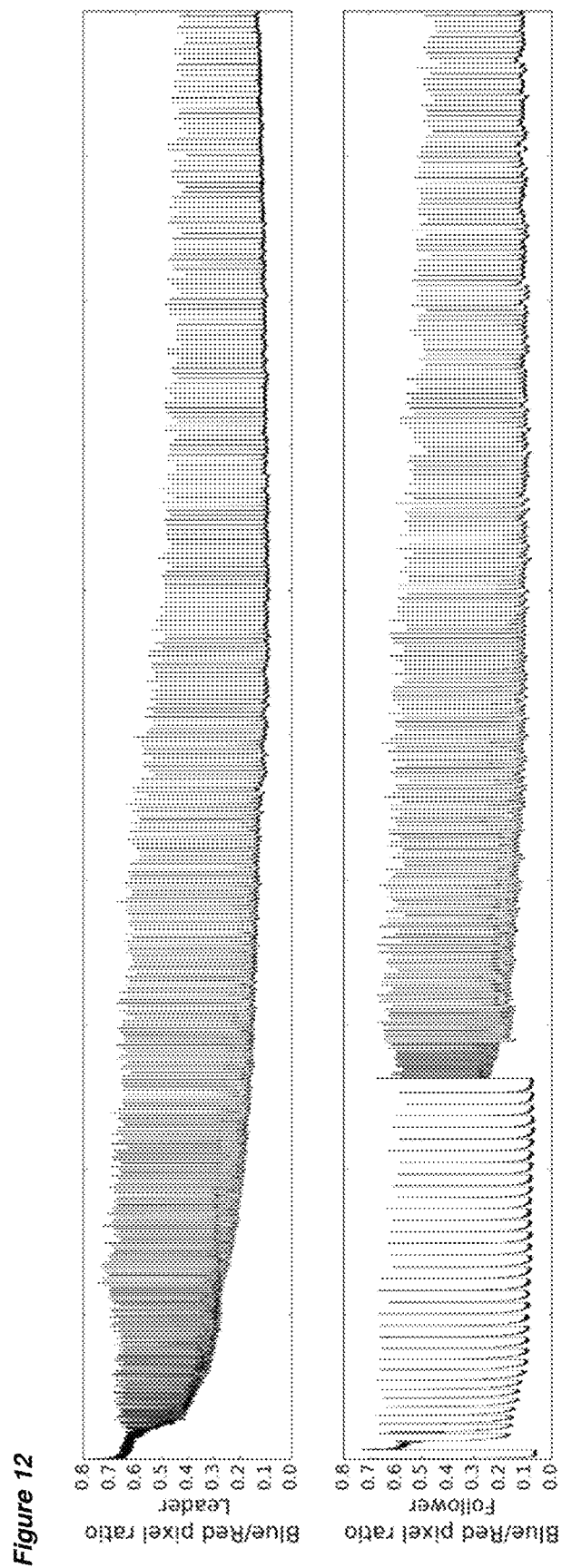
Figure 12:
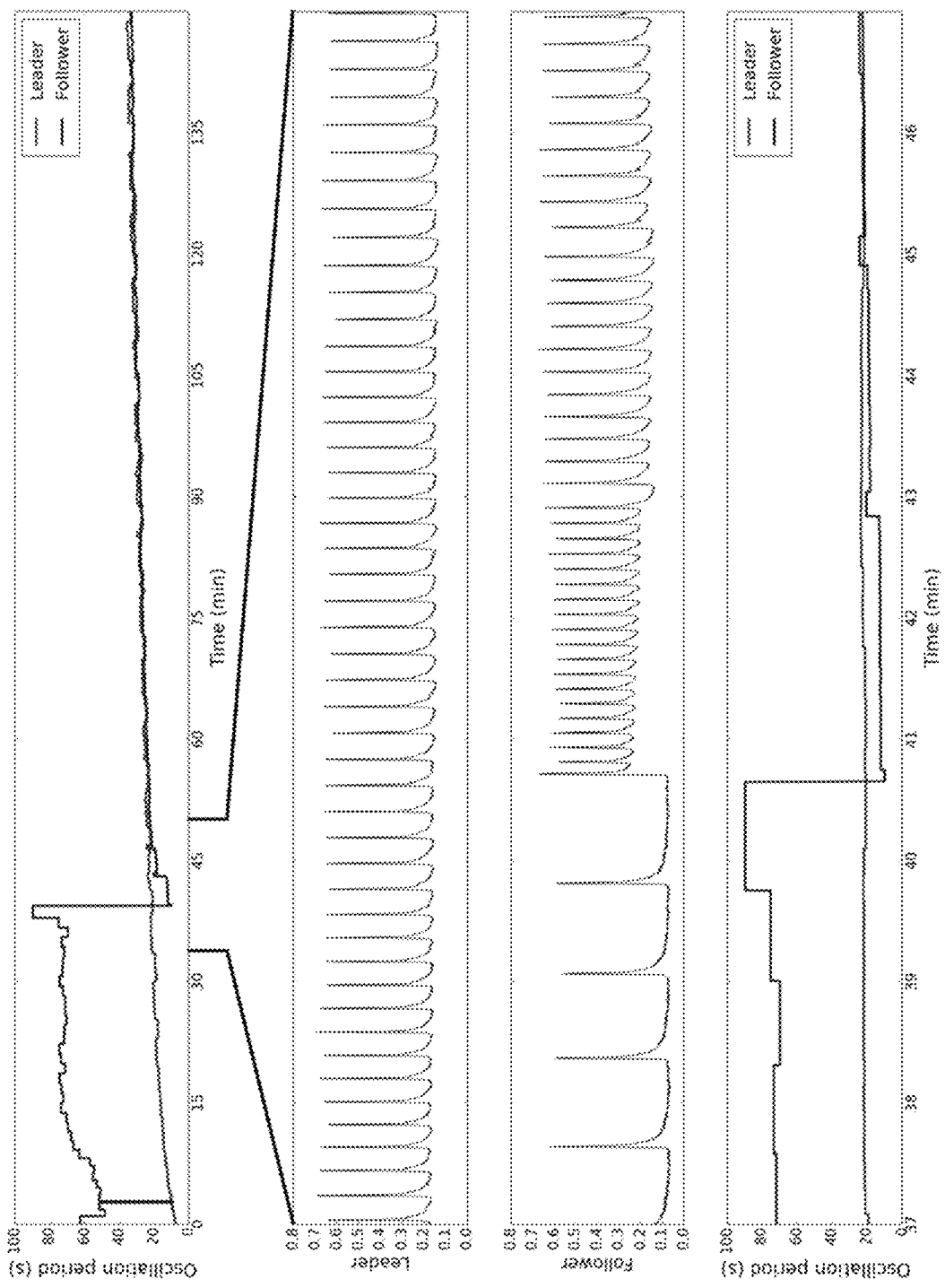

FIG. 12 shows the change in the relative blue/red pixel ratio over time (min) for BZ oscillation reactions performed by two synthesisers in a system according to an embodiment of the invention, where the change in ratio is shown for the (top) leader synthesiser and (second from top) the follower synthesiser, and the change in ratio is also shown for a period within the experiment for the (third from bottom) leader synthesiser and (second from bottom) the follower synthesiser; and also shown is the change in the oscillation period (s) over time (min) for the leader and follower synthesisers (third from top), and the change in the oscillation period also shown for a period within the experiment for the leader and follower synthesisers (bottom).

Figure 13:
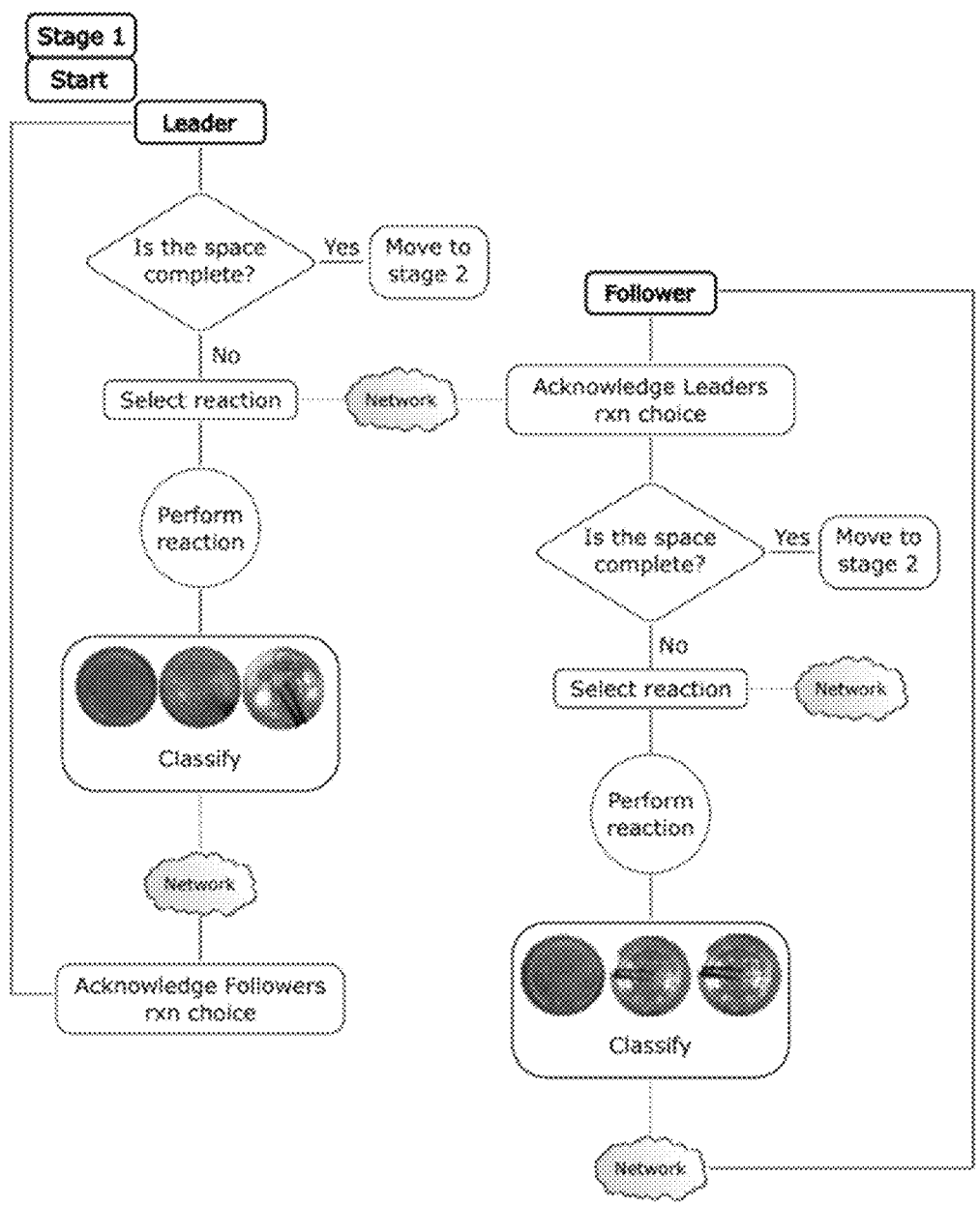
Figure 13:
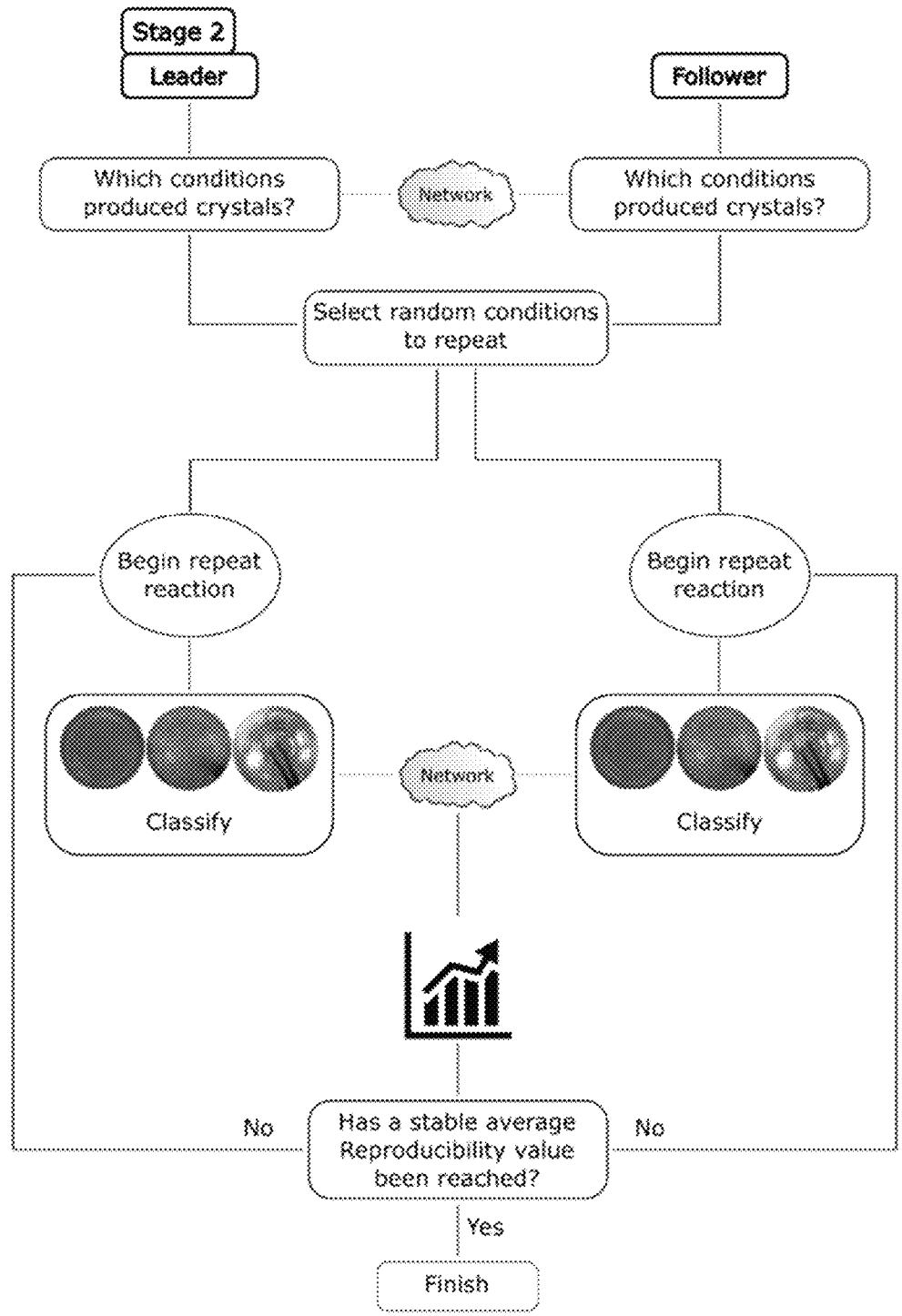

FIG. 13 shows (left) a flow diagram for the first stage of an algorithm for collaborative chemical space exploration using a system according to an embodiment of the invention, where two different reaction parameters are tested by two synthesisers; and (right) a flow diagram for a second stage, which is a series of reactions repeating the crystal-yielding reactions from the first stage, to assess their reproducibility.

Figure 14:
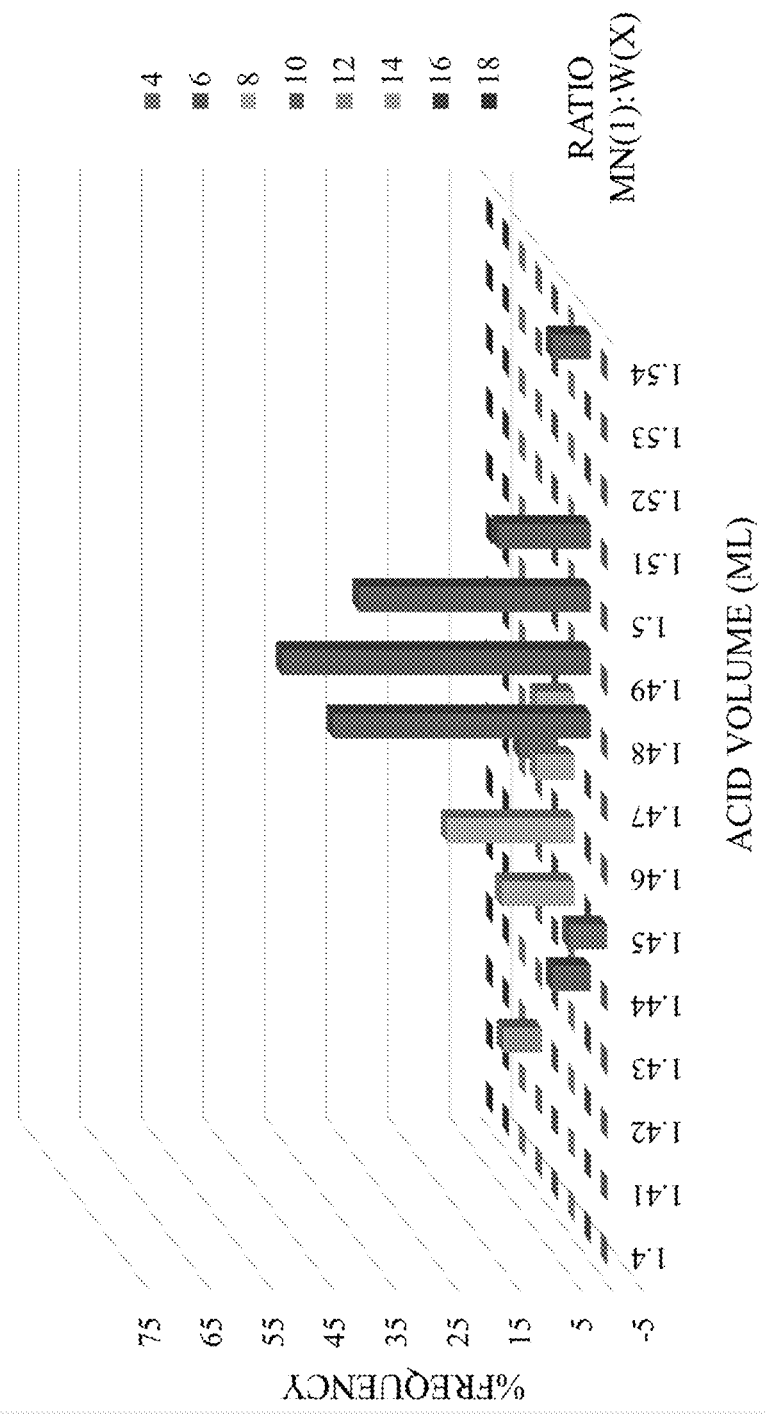

FIG. 14 shows the percentage frequency of crystal formation with change in acid volume (mL) and change in Mn and W (mole ratio) in a series of polyoxometallate preparations, in a scan of available reaction space using a system according to an embodiment of the invention comprising a plurality of synthesisers.

Figure 15:
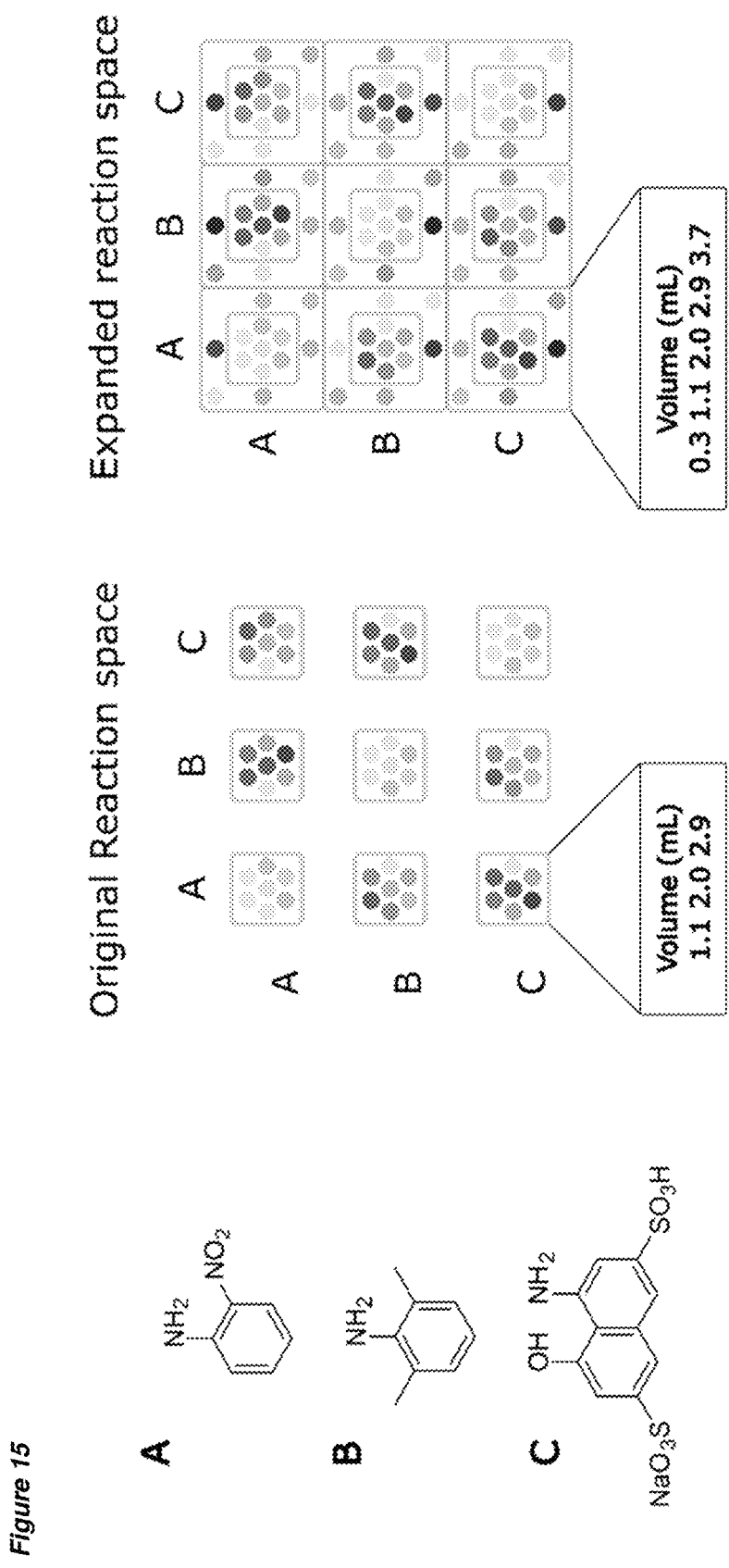

FIG. 15 shows (left) the aniline derivatives used in the game embodiment of the invention; (middle) the original shared reaction space available to the game players; and (right) the expanded shared reaction space available to the game players after the first round of the game is completed.

DETAILED DESCRIPTION

The present invention provides a cooperative system for use in automated chemical or biological synthesis. The system comprises a plurality of synthesisers that are in communication via a communal reporting platform.

The inventors have shown that a network of automated synthesisers is capable of performing chemical reactions, analysing them and using the internet to communicate data.

The system may be used in synthesis, discovery, and assessing reproducibility.

The present inventors have established that the connection of automated synthesisers capable of doing chemical reactions in real-time by the internet provides novel approaches to explore many chemical reactions, assess reproducibility, and control complex chemical reactions in real time.

Conceptually the system of the invention includes a chemical-cloud which holds a code to control a number of identical automated synthesisers, or robots. This code may be held remotely or distributed to all the robots. By sharing a common hardware, list of chemical reactions, and code, the robots can collaborate by doing common chemical tasks simultaneously but decentralised over several laboratories in different locations (see FIG. 1).

Similar to the world of distributed and cloud computing, the present invention can act as a cluster system to explore large chemical space by distributing the workload across the robots connected to the network (see Prabhu et al.). The results can be easily reproduced anywhere and anytime by a similar machine, greatly increasing the reliability of chemical research allowing instantaneous validation of new procedures and discoveries (see Kitson et al.).

The principle of multi-threaded networking of individual automated synthesisers, such as chemical robots, can be shown by considering simulations of related strategies using an agent-based modelling approach (see FIG. 2). Here, each agent represents a synthesiser as an entity that does all the possible reactions until the goal is achieved. In the random strategy, the most basic approach, each synthesiser has no memory of the reactions attempted. In contrast, an approach where the synthesiser has memory of the previous reactions increases the probability of finding the goal in the next move, and when the number of synthesiser is increased, and they can see the history of all the previous moves, all the synthesiser can work together collaboratively solving the problem most quickly (see FIG. 2a). As the number of robots increase the searches are easier, and the collaborative approach also wins (see FIG. 2b).

For many chemical and biological searchers, the brute force exploration of many different combinations of reagents and concentrations is a powerful way to optimize a reaction, or to discover new reactivity. In recent years much of this workload can be automated in the laboratory, but the individual work-sites are isolated from each other. The present work shows that by networking two or more automated synthesisers capable of doing a given set of reactions, the synthesisers may collaborate with each other, even if they are physically separated over a range of different sites anywhere in the world.

The systems exemplified herein are purposely simple. Nevertheless, the systems are capable of managing three completely different chemical processes, all involving collaborative approaches based on data sharing. Thus, in one example, a combinatorial grid of organic molecules was rapidly explored, looking for a specific result, showing the advantages of multiple units.

By using the real-time communication, the periods of two oscillating reactions were precisely controlled used a system of the invention, and this system was used to encode and decode information. In a further exemplification, two synthesisers performed and reproduced polyoxometalate syntheses under varied conditions in order to assess the reproducibility percentages of different reaction parameters.

From this work, the inventors have understood that the systems of the invention provide an expansion in automated systems inside chemistry laboratories, where automated synthesisers can be used to repeat standard procedures, which will allow chemists more time for the creativity. A network of such robots in distant laboratories is easily scalable and may develop into a worldwide system with thousands of synthesisers connected. This would increase exponentially the productivity and reliability of research.

In the present case each system has a plurality of synthesisers, each with its own controller. That controller provides reaction information to, and receives reaction information from, the common reporting platform. The controller is responsible for the operation of the synthesiser, and it coordinates the reagent delivery system, the reaction of those reagents within the reaction vessel and the analysis of the reaction products. On the basis of this interaction with the reporting platform, each synthesiser can uniquely perform its own experiments, and may do so independently of the other synthesisers in the system.

The prior art generally describes systems where a single controller is combined with a device for storing information, and that single controller has responsibility for all the reaction vessels. There is no use of individual controllers to control reaction vessels within separate synthesisers, and there is no disclosure in the prior art that a controller communicates via a communal reporting platform, such as a remote reporting platform.

US 2016/0288081 describes a single reaction system made up of a series of parallel reactors. The products produced in a reactor may be analysed. The system is controlled by a single control system, and there is no mention of individual synthesisers each having a separate controller. There is no mention anywhere of a reporting platform for coordination of reactions between different synthesisers. There is also no reference anywhere to information feedback to and from the synthesisers to control future reactions within the system. This document describes a unified synthesiser under the management of one controller, and that system interacts with no other.

Similarly US 2008/0286174 primarily describes a single synthesiser having multiple parallel reaction vessels. The possible use of multiple synthesisers in parallel is mentioned. However, there is no description here of any interaction between an individual synthesiser and a communal reporting platform. The multiple synthesisers are also serviced by a single robot under a single control system, and they are not individually controlled, separate from other synthesisers.

US 2003/012700 also describes a reaction system having parallel reactors within a single synthesiser. There is no mention of independent synthesisers communicating through a communal reporting platform.

US 2018/0010058 describes apparatus and methods for investigating naphtha reforming processes. Although the system is shown having multiple reactors, these are under the sole control of a single controller. There is no suggestion that the system could take the form of multiple independent synthesisers that communicate with a common reporting platform.

GB 2372506 describes a system for managing the operation of multiple reactors. Each of these reaction vessels is managed by a single control system, which chooses the reaction to be performed within each reactor according to a search of a reaction database. As with documents discussed above, there is no disclosure of a reactor being independently controlled by its own controller, and there is no reporting to and from a communal reporting platform by multiple controllers.

Exemplary and preferred synthesisers and reporting platforms are described in further detail below, together with a description of their use in chemical and biological reactions.

Synthesisers

A synthesiser is an automated reaction system for use in chemical and biological synthesis, with the synthesiser comprising a reaction vessel for chemical or biological reactions and an analytical system for analysis of a reaction mixture or components from the reaction mixture, including a reaction product.

The synthesiser includes a reaction vessel for the performance of a reaction within. The reaction vessel is not particularly limited and it may be chosen with the intended chemical or biological reaction in mind.

The reaction vessel may be, for example, a reaction flask, such as a round-bottomed flask, a reaction cartridge, a vial, or a flow reactor, amongst others.

The synthesiser may be provided with a single reaction vessel, and this reaction vessel may be emptied after the completion of each reaction, and subsequently reused for a later reaction.

A synthesiser may be provided with a plurality of reaction vessels, where each reaction vessel may be used for the performance of a single reaction. Alternatively, the plurality of reaction vessels may be for use in a multi-step synthesis, where each reaction vessel is for performance of a reaction within the multi-step synthesis. The synthesiser may be provided with means for transferring the contents of one reaction to another reaction vessel.

Preferably, the reaction vessel is suitable for use within an automated synthesis system, and is suitable for use with a fluid and solid transfer apparatus, where such apparatus is for the delivery of reagents, catalysts and solvents into the reaction vessel, as well as the removal of materials from the reaction vessel, for example after reaction completion.

For example, a synthesiser may be provided with syringe pumps for the delivery of fluids into a reaction vessel, and a synthesiser may be provided with a syringe pump for removal of material from a reaction vessel, for example to ready the reaction vessel for use in a further reaction.

The synthesiser is provided with an analytical system which is adapted to analyse the reaction undertaken, including the analysis of the reaction product. The analytical system is accordingly provided with one or more sensors which are suitably located to analyse the reaction mixture, or any component removed from the reaction, either during the reaction or at reaction completion.

The nature of each sensor in the analytical system is dictated by the reaction to be performed and the reaction product, as well as the reaction parameters that are under consideration.

The sensors for use in the present case are not particularly limited.

In preferred embodiments of the invention the analytical system includes a camera suitable for recording still and/or video images. The camera is typically suitable for recording images in real time, and is typically capable or recording images in colour, grayscale and black and white.

The analytical system may report the recorded analytical data from a sensor directly to the reporting platform, where such may be made available to other synthesisers to access and interpret.

The analytical system may also be provided with a processor for the interpretation of the analytical data recorded from the sensors. The processer may be provided to analyse the analytical. Here, the processor generates a report of the analytical data for posting to the reporting platform. Thus, in some cases it is not necessary for the synthesiser to report all the recorded data from the sensors, a portion of that data may be report, or a summary or conclusion of the data may be reported.

The sensors used in the present case are preferentially those capable of developing and sending real time relating to the reaction to the reporting platform, via the controller. The rapid generation and posting of reaction information to the reporting platform ensures that other synthesisers in the system are provided with a prompt summary of a synthesiser's work.

It is also the case that synthesiser may report to the reporting platform the detailed analytical data together with its interpretation of that, so that both are available for inspection by other synthesisers.

The present invention may allow synthesisers to, and preferably does, make use of social media for reporting to. Many common and well-used social media applications are based on the sharing of imagery, such as still camera and video images, and text, often in a character-limited manner.

Each synthesiser is therefore preferably adapted to report to a reporting platform, such as one that is in the form of a social media application, with images, still or otherwise, and with short information texts. As noted above, a synthesiser may be provided with a camera for recording still or video images of a reaction, and these images may be posted directly to the reporting platform.

A short information text for posting may be concise information about the reaction progress or outcome that usefully characterises that reaction and its product, taking into account the interests and desires of the user. Thus, the short information text posted to the reporting platform may relate to beneficial properties of the final product, such as yield, colour, molecular weight, activity, and so on. The short information text for a reaction may be provided as a graded property to allow differentiation with the short information texts reported by other synthesisers.

The synthesiser is also provided with a controller for managing the performance of a reaction within the reaction vessel, and for collecting the analytical data and reporting it to the reporting platform. The controller is also capable of accessing data from the reporting platform. This accessed information may be used to guide future reactions for the synthesiser to perform.

Each synthesiser is provided with its own controller. Thus, the system has a plurality of synthesisers, and therefore a plurality of controllers. The operation of a controller to individually control the operation of the synthesiser is discussed in further detail below.

A system of the invention comprises two or more synthesisers, such as two, three or four or more synthesisers.

The synthesisers may be prioritised within the system, with one synthesiser deemed the priority synthesiser. Other synthesisers in the system may be deemed equal, or they may be ranked also, and ranked beneath the priority synthesiser.

A priority and ranking system may be provided in order to avoid the possibility of repetition within the system. Where two or more synthesisers post an intention to perform the same reaction, the priority or higher ranked synthesiser is permitted to perform the reaction whilst non-priority or lower ranked synthesisers are obliged to make a another selection for reaction within the available chemical space.

In alternative embodiments, the synthesisers are deemed equal, and occasional repetitions within the system may be permitted, where two or more synthesisers post an intention to perform the same reaction at the same time.

Each synthesiser may be provided with permission to explore the full scope of the chemical or biological space under consideration. Here, it is the case that each synthesiser may be provided with the full range of reagents needed to access that scope of chemical or biological space.

Together a plurality of synthesisers may be used to collaboratively explore a chemical space. Thus, for a particular reaction, the synthesisers may together investigate each possible reagent combination, or they may together investigate each possible reaction condition.

Each synthesiser, through its controller, is capable of choosing reactions for performance. Here, the choice of reaction to be performed may be a random choice from the available reactions. Alternatively, the choice of reaction to be performed may be a methodical choice, which is based on a simple step change from the previous reaction performed by the synthesiser. Thus, there may be a change in a single reagent, or there may be a change in a single reaction parameter. Subsequent reactions may then follow this pattern of changes in single reagent and changes in single reaction parameter. In a further alternative, a synthesiser may select a future reaction for performance based on an algorithm, such as a genetic algorithm, or any such algorithm that looks to pursue combinations of reaction features, such as reaction chemical and physical inputs, that are associated with beneficial results.

A synthesiser may use a combination of these approaches to select future reactions for performance.

In the present case, a synthesiser may report to the reporting platform with prior to and after the performance of a reaction. In a first step a synthesiser selects a reaction to perform, and synthesiser posts the details of this intended reaction to the reporting platform for approval by the reporting platform. If the reaction is approved, the synthesiser performs the reaction, and then subsequently reports the results of the reaction to the reporting platform. The results of the reaction are the results presented to the reporting platform from the analytical system via the controller as noted above.

If the reaction is not approved, a synthesiser is obliged to propose a different reaction for performance, differing from the reactions previously proposed. A synthesiser will continue to propose reactions until a reaction is approved.

A synthesiser will continues to propose and perform reactions until such time as the available reaction space is deemed suitably explored. Here, the synthesisers may continue to operate until all available reagent combinations or reaction condition combinations have been utilised.

In other aspects of the invention there is provided a multisystem comprising a plurality of systems according to the present invention. Here, a reporting platform of one system may be shared as the reporting system of another system. Alternatively, a plurality of reporting platforms may be provided which are in comminution with each other to share reaction information from each system.

The system may be programmed such that a system within the multisystem independently explores the same available reaction space as another system in the multisystem. In this way, one system may be used to validate the results of another system or otherwise. Here, the systems may be used to probe the reproducibility of reactions, for example to identify reactions whose outcome have a high probability of success, and thereby to identify chemical and physical inputs that are associated with success, and also associated with lack of reproducibility and also failure.

As noted herein, a single may also be suitably programmed for validation of reaction results by reproducing the same reaction multiple times within the system, using different synthesisers, preferably, but also allowing a single synthesiser to repeat reactions.

A multisystem may also be used to share the workload from one system across multiple systems, thereby reducing the work burden on one system. The work in the system may be decentralised, with each system apportioned a unique area of the available reaction space. Each system may then independently explore that reaction space, with reporting to its reporting platform, which platform allows sharing of information amongst all systems in the multisystem. The work in the system may be broadly shared, with every system in the multisystem having access to the entirety of the reaction space. As within an individual system, the multisystem provides allows the reporting platforms to work in collaboration to allow the exploration of the reaction space without undue repetition, or preferably without repetition.

The multisystem may have individual systems dispersed across multiple locations, and the synthesisers in each system may similar be dispersed across multiple locations.

Reporting Platform

The system of the invention is provided with a communal reporting platform. The reporting platform may take the form of a data storage unit, such as a server, to which all the synthesisers have access to, and are communicable with.

The reporting platform is typically located remotely from each synthesiser. Thus, the reporting platform is not provided in a laboratory with any one synthesiser within the system.

The reporting platform may not be provided at a single physical location, and the storage function, together with any processing functions, may be located at multiple locations, which locations may be unknown to the use, for example where the reporting platform is hosted within the cloud, or hosted by a third party data and processing provider.

A synthesiser may be in communication with the reporting platform through wired and/or wireless communication.

The systems and methods of the invention may make use of social media as the reporting platform. Current examples of social media for use include Twitter, Facebook, Linkedin, Snapchat, Instagram and the like.

A reporting platform for use, such as a social media, may be characterised by the ability of the platform to receive, store and display reaction information from a synthesiser, such that this reaction information is accessible to all other synthesisers in the system. The reporting platform is preferably able to make reaction information available in real time, as soon as it is delivered to the platform from a synthesiser.

The sending of information to the reporting platform, and its subsequent availability for review may be referred to as posting of the reaction information. Such terminology is used, for example, with the Facebook platform. In other platforms, different terminology may be used to refer to the delivery and display of information. For example, the Twitter platform refers to such processes as Tweeting.

The information provided by a synthesiser to the reporting platform, and therefore the information made available by the platform to other synthesisers may in the form of code, plain text, or visual data, or a combination of these, or other information vectors.

Many social media platforms favour the posting of limited amounts of information, or they operate most usefully where limited amounts of information is posted. For example, the Twitter platform allows text posts that are currently limited to 280 characters.

In a preferred embodiment a reaction outcome may be posted as an image or video, optionally together with a text report of the reaction outcome.

The information posted to the reporting platform is typically not the full data profile recorded by the analytical system. Instead, the synthesiser may report a result that is representative of the reaction outcome. For example, the synthesiser may report a reaction yield, or a property of the reaction product, such as colour or the relative or absolute amount of a characteristic analytical signal.

Each synthesiser is capable of reading data held by the reporting platform, and the synthesiser is capable of selecting a unique future reaction for performance based on the results reported to the reporting platform.

The reporting platform is adapted to receive from each synthesiser information relating to an intended reaction. The reporting platform collates this information and provides the collated information to all synthesisers in the system to access.

It follows that the reporting platform is provided with a control system for handling incoming data, arranging this data and storing that data in accessible format. The controller allows the data to be displayed and accessed by all synthesisers.

The control unit may also provide security within the system, and may control access into the reporting platform and may control access to the posted data. Thus, in one embodiment the control unit may privatise posted data, and this data may only be available to synthesisers within a private system. It follows also, that in some embodiments, only accredited synthesisers may be permitted to post to the reporting platform also. Thus, the system may operate without publication of the reaction plans or the reaction results.

In other embodiments, the posted data to the reporting platform may be publically available, however the reporting platform may still nevertheless prevent unauthorised synthesisers from participating in the system.

In yet further embodiments, the system may be entirely open, and any synthesisers wishing to participate in the system may be permitted to do so.

The controller in the reporting platform may be provided with a clock to time stamp the inputs that are posted to it. This may be of most importance where the synthesisers are posting their intended reactions to the system. The synthesiser that posts first in time for an intended reaction may be given exclusive permission to perform that reaction compared with those synthesisers that post the same intended reaction later in time.

A synthesiser may be prioritised within the system, and where different synthesisers post their intention to perform the same reaction, a synthesiser having a higher priority will be granted permission to perform the reaction over a reporting platform having a lower priority.

The system is suitably programmed with an intended reaction plan which defines an available reaction space. The reaction plan is shared with the synthesisers, and this may be done via the reporting platform, which may also hold and make available the reaction plan. Synthesisers added to the system, for example during the operation of the system, may be provided with the reaction plan, together with a summary of the reactions performed to date according to the reaction plan.

Methods and Uses

The system of the present invention may be used in methods of synthesis, for example to prepare chemical and biological products.

The system may be used to explore an available chemical reaction space through the cooperative workings of linked synthesisers. The system of the present case is a network that allows for information to be shared between synthesisers that are linked through a communal reporting platform.

The methods of synthesis described herein involve a plurality of synthesisers sending and receiving data to and from a reporting platform.

There is provided a method of performing a plurality or reactions, the method comprising the steps of:
  (i) providing a system according to the first aspect of the invention, where the system comprises a plurality of synthesisers that are in communication via a communal reporting platform;
  (ii) permitting each synthesiser in the system to perform a reaction;
  (iii) allowing each synthesiser to post a reaction result to the reporting platform; (iv) allowing each synthesiser to observe the combined reaction results posted on the reporting platform; and
  (v) permitting each synthesiser to select a future reaction for performance, where that future reaction optionally differs from the reactions previously reported by all synthesisers to the reporting platform.

Within the method, a plurality of reactions defines a reaction space which is derived from the combinations of a series of set chemical and/or physical inputs into a reaction, and the method explores at least part of the available reaction space by performing each of the possible reaction utilising the combinations of set chemical and/or physical inputs, wherein the exploration of available combinations of set chemical and/or physical inputs is shared between available synthesisers.

A synthesiser may perform, and may only perform, a reaction that are not performed by any other synthesiser in the system.

Step (ii) may further comprise a check of the reported intended syntheses, and an individual synthesiser or the reporting platform provides an approval or disapproval of an intended synthesis, based on an analysis of all reported intended syntheses and reaction results.

As noted previously, a first synthesiser may have priority status over a second synthesiser, and the first synthesiser is permitted to perform an intended reaction in preference over the second synthesiser.

In in a preliminary step, each synthesiser may indicate to the reporting platform which chemical and physical inputs are available for use with that synthesiser.

The methods of the invention permit a system to explore a reaction space, and in doing so the system may identify chemical and physical inputs into the reaction space that are associated with beneficial results, and also results that are not beneficial. Where, the system identifies beneficial results, the system may repeat the reactions leading to those beneficial results in order to validate the result.

Generally, the systems of the invention may be used to investigate the reproducibility of results within the reaction space, and the system may be permitted to allow a synthesiser to repeat work previously performed within the system. Thus, in the methods of the invention step (v) may alternatively permit each synthesiser to select a future reaction for performance, where that future reaction either differs from the reactions previously reported by all synthesisers to the reporting platform, or the future reaction is a repeat performance or a reaction previously reported to the reporting platform.

Preferably, the system is programmed to allow the repetition of a reaction a limited number of times. For example a reaction may be repeated at most once, twice or thrice.

Preferably, a reaction is repeated only if it is associated with a particular reaction outcome, such as an outcome that is associated with a benefit or desirable outcome. In this way, the system does not repeat reactions that are known to not work, or to otherwise produce undesirable results.

The methods of the present case allow collaboration between synthesisers. Here, synthesisers may work in tandem to explore available reaction spaces. The exploration of the space may be methodical, with the system working through the available combinations of physical and chemical inputs.

As noted previously, the system may also be programmed with an algorithm, such as a genetic algorithm, to analyse results and to direct future intended reactions by the synthesisers to focus on reaction conditions that are associated with beneficial results. The direction of future reactions may be provided by a controller in an individual synthesiser, with each synthesisers independently deciding on an optical approach to choosing reactions.

However, the system may work collaboratively in this respect too, with the intended reactions directed by a communal controller, which may be provided as part of the reaction platform, or as part of a priority synthesiser, which communicates with each synthesiser in the system.

The system also allows individual synthesisers to compete within the system to explore the available reaction space. Here, the results from synthesisers are compared at stages of the exploration of the chemical space, and the synthesiser that has produced the most beneficial result at that stage is deemed a winner, and is permitted to continue exploring the area of chemical space that was associated with that benefit. The synthesisers that have not produced a beneficial results are deemed losers, and these synthesisers are required to change their strategy for exploring the available reaction space. For example, the synthesisers may be required to move way from certain chemical and physical inputs, and they may be required to focus on the area of reaction space explored by the winner, or they may be require to explore another reaction space entirely.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

Experimental and Results

The following examples are provided solely to illustrate the present invention and are not intended to limit the scope of the invention, as described herein.

For use in the present invention, a system was designed around a low power single board PCduino computer running the Linux Ubuntu operating system (as described in detail below). A software platform was also built using Python, to control the robot (automated synthesiser) and its sensor system (analytical system).

The liquid handling contained a number of peristaltic pumps connected to a driver board and the sensor array is a single web cam connected to the PCduino via USB. Both the hardware and the software are modular and could be easily upgraded to include other chemical effectors and sensors. By using a common software base, it was possible to tailor the system for a particular chemical problem, combining the three main parts of the robot with related external reporting platforms (see below).

Communication was achieved via a network (Wi-Fi or ethernet) connection so the robot could broadcast its state and communicate with the other units. As a proof of concept all communication was conducted through the Twitter platform or by a bespoken server system. The data collected was analysed locally on each board and sent as plain and readable text to the Twitter account or server. In this way the posts were then acquired and processed by any other board on the network.

For the work described here, a total of six identical automated synthesisers were built. The reactions were performed in a flask with magnetic stirring, with each flask washed and reused for each experiment.

1. Robot Design and Concept:

The robot computational core was a PCduino running the Linux Ubuntu operating system, which executes homebuilt code in python to control pumps and a webcam. Access to internet is achieved via a WiFi connection. For everyday use the board was connected also to a monitor, mouse and keyboard. Liquid handling was performed by a set of peristaltic pumps, the pumps were turned on for duration of the required addition time. The pumps were connected through Tygon® tubing with the reagents and the reaction flask. Generally five pumps were dedicated to adding the reagents, one adding water for washing and the last one to empty the reaction flask. Data was acquired with a USB webcam capable of recording images and video from the reactions. The reactions were performed in a standard 14 mL glass vial. The reaction mixture was magnetically stirred with a home built stirrer using a small fan.

The robot was designed to be as simple and affordable as possible. It could be assembled in just few hours.

1.1 Peristaltic Pumps

The control over the solutions was performed using a set of peristaltic pumps. The pump was driven by a 12 V DC and it was connected to the driver board mounted on pcDuino. In this present work model KFS-HB2B06M was used, where M was either R, B, G, P which refers to pump colour (Red, Blue, Green, Purple respectively).

The pumps were designed to have a flow rate of 4 mL/min towards a single direction. Since a loss in precision over time was noticed the pumps were recalibrated every week and after any maintenance operation.

1.2 pcDuino Board

The robot ran on a pcDuino3, powered by a 5V (2A) power supply fed through a micro USB cable. This board contained the following:
- CPU: AllWinner A20 SoC 1 GHz ARM Cortex A7 Dual Core
- GPU: OpenGL ES2.0, Open VG 1.1 Mali 400 Dual core
- 1 GB DRAM, Onboard Storage: 4 GB Flash memory, microSD card slot (supports up to 32 GB)
- Arduino style Peripheral headers
- HDMI Video output
- SATA socket, IR receiver, LVDS LCD interface and MIPI camera interface
- Audio out: 3.5 mm Analog Audio and 12S Stereo Digital Audio
- USB interface
- RJ45 Ethernet Connection 10M/100 Mbps and Wi-Fi module
- API interfaces such as UART, 6xADC, 2xPWM, 14xGPIO, 1xI$^2$C, 1xSPI More details and further information regarding the pcDuino platform can be found at http://www.pcduino.com/wiki/index.php?title=Book 1.3 Power Supply Unit The robot was powered by a 5 V (2A) DC power source. However, the Peristaltic pumps were driven by a 12 V (1A) DC source. In this work, a 500 W ATX power supply unit was used.

1.4 Software

The PCduino ran with the Ubuntu operating system. The platform was controlled by a dedicated program written in python. Due to specific experiments each project part was completed by using a dedicated program. However, the low level software was the same and was composed by three main parts with respective external libraries:

Pumps control: used gpio, a common library to control the pins of the pcduino, and therefore operation of the pumps. Since there was no feedback from the pumps, a code converted the amount of solution to be pumped into the running time of the pump. It was based on a calibration process where the flow rate of each pump was tested and saved.

Within the organic reactions, the pumps control was responsible for reagent mixing, dilution and the cleaning cycles. Within the physical reactions, the pumps control was responsible for reagent mixing, real-time additions and the cleaning cycles. Within the inorganic reactions, the pumps control was responsible for reagent mixing, mixture transfer between vessels and the cleaning cycles Webcam control: was based on the opencv library. It had access to the webcam and provided images and videos of the reaction. Further image/video analysis is discussed below.

Within the organic reactions, the webcam control was responsible for frame saving, colour detection and colour difference calculations. Within the physical reactions, the webcam control was responsible for real time video processing, oscillation period calculations, and blue pixel count saving. Within the inorganic reactions, the webcam control was responsible for video recording, crystal and precipitate detection.

Network management: used the twython library and controlled the networked part of the platforms. It allowed the platform to update its state by sending a tweet on its account and to scan a Twitter account for synchronization and collaboration.

Within the organic reactions, the network management was responsible for shared chemical space exploration and game playing. Within the physical reactions, the network management was responsible for oscillation period synchronisation and message encoding. Within the inorganic reactions, the network management was responsible for chemical space exploration and reproducibility assessment.

Coordinator: the software core of each project section was a "coordinator" program. It managed all the experiment components: physical reactions, image analysis, network synchronization and search algorithm.

2. Organic

To realise the system and methods of the invention, the present inventors deployed robots to explore a reaction grid forming a range of dye colourants looking for a set of specific colours (see Gung et al.). The robots, or automated synthesisers, would mix two different reagents together in a clean sample vial, and the results of each reaction were automatically recorded with a webcam, analyzed and posted in real time to Twitter. By allowing each synthesiser to read the Twitter feed, the synthesisers were able to collaboratively search the available reaction space, thereby reducing the total number of experiments required by each synthesiser to reach the goal of exploring the entire colour space.

During the chosen reaction, two aniline derivatives were mixed with sodium nitrate in an azo-coupling reaction. After ca. 30 minutes the synthesis of the azo compound could be confirmed by a colour change, and the colour of the solution was recorded and analysed in real time. To cover the largest number of distinct colours using the least number of starting materials, three aniline-derivative were selected: o-nitroaniline, 2-6-dimethyl-aniline and sodium 4-amino-5-hydroxy-2,7-napthalenedisulfonate hydrate. Each starting material was used as both a first component (to synthetize the diazonium salt with the amine group) or as the second component (for the substitution on the benzene ring). The nine molecules obtained from the grid (left-hand side of picture 3) was expanded further by using 13 different ratios for each reaction, obtaining 117 possible combinations. Due to the chemistry involved, some of the molecules synthetized acted as pH indicators, therefore a fixed amount of base was added after each reaction to check for a colour change.

Overall, the time for each reaction including cleaning and dispensing was around 40 minutes, and during each experimental cycle the algorithm was designed to select a random reaction and share the chosen parameters via Twitter or the server. Next, the system then performed the reaction selected and saves four representative images of the reaction which were analyzed locally and shared online. A parallel background process checked the other robots every 5 minutes for Tweets and updated the database with the results respectively. This allowed both synthesisers to have the same data stored in their internal databases, avoiding doing the same reaction twice.

The search was successfully run several times, and this shows that the average number of reactions to find the rare blue colored one is halved. Also, during the exploration of the full grid, some unexpected colours were observed e.g. green and pink, which are rarely associated with azo-dye motifs (see FIG. 4).

2.1 Experiment Protocol

The selected organic reaction for study was an azo-coupling reaction. The starting materials were two aniline derivatives and sodium nitrate. During each reaction, the first aniline derivative (1) was mixed with sodium nitrate (2) to form the relative diazonium salt (3). After 2 minutes the second aniline derivative (4) was added to the solution. After a period of between 1 and 60 minutes the synthesis of the azo compound (5) was observed by consideration of the observed colour change.

The reaction is an electrophilic aromatic substitution reaction where the aryldiazonium cation is the electrophile and the benzene ring of the second aniline is the nucleophile (see Scheme 1).

Scheme 1.

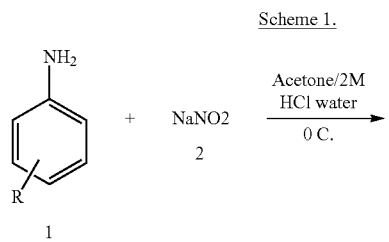

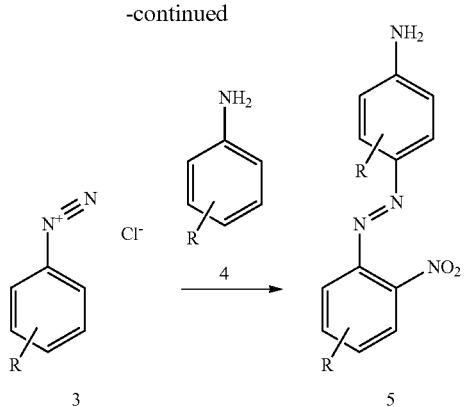

In order to cover the largest variety of colours with the less amount of starting materials three aniline-derivative were selected: o-nitro-aniline (6), 2-6-dimethyl-aniline (7) and sodium 4-amino-5-hydroxy-2,7-napthalenedisulfonate hydrate (8).

Each starting material could be used as a first component (to synthetize the diazonium salt using the amine functionality) or a second component (for the substitution on the benzene ring). As a result, a 3×3 reaction grid was performed, obtaining a variety of coloured products. The products and their colours are set out in Table below (images of products not shown here).

In order to have a larger chemical space to explore, each reaction was further expanded using different reagents ratios. Five possible volume ratios (0.3, 1.1, 2.0, 2.9, and 3.7) were chosen, and each reaction was expanded using all combination of these ratio for the three components, maintaining a total reaction volume of 6 mL:

[0.3, 3.7, 2][1.1, 2.9, 2][2.9, 1.1, 2][3.7, 0.3, 2][0.3, 2, 3.7][1.1, 2, 2.9][2.9, 2, 1.1][3.7, 2, 0.3] [2, 0.3, 3.7][2, 1.1, 2.9][2, 2.9, 1.1][2, 3.7, 0.3][2, 2, 2]

Nine possible reactions of the first grid was expanded with thirteen possible reagent ratios, obtaining a 117 reaction space. The expanded reaction scheme is shown.

Scheme 2.

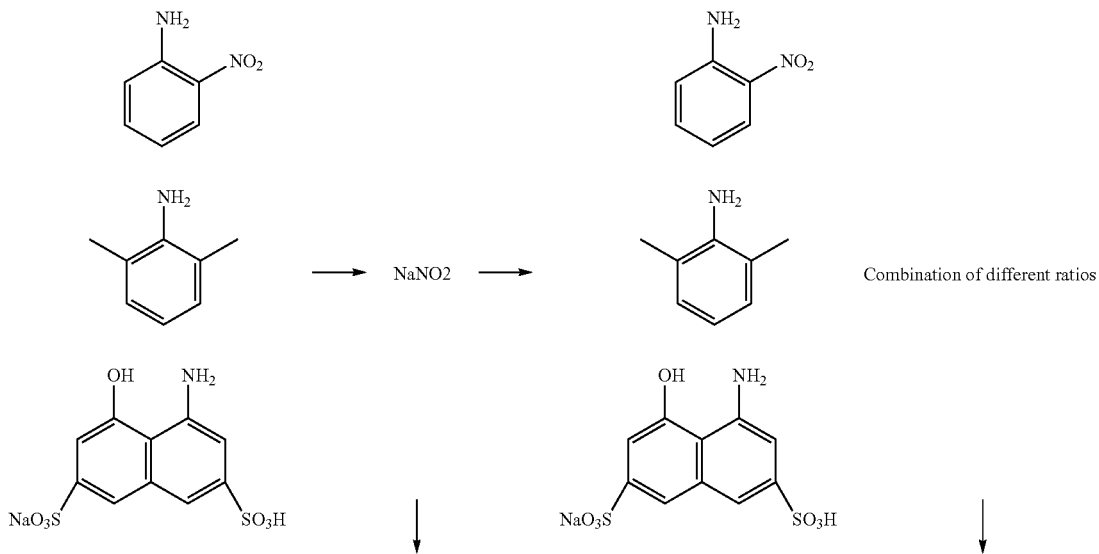

9 Possible Reactions ⎫
⎬ 117 Reaction Grid
13 Possible Reactions ⎭

Since the products often acted as pH indicators, additional colours could be obtained by adding a basic reagent to the product mixture after the reaction as complete.

2.2 Image Analysis

The organic part of the project focused on the product solution colour. Thus, the product colour was recorded as an image frame using the webcam. The recorded image frame was converted into hsv colour domain. Through a calibration process, each colour was associated to a specific hsv range value. In each experiment a region of interest was analysed and the pixel values were compared with the colour ranges. The colour with the highest pixel count was considered the solution colour (red, orange, yellow, blue, colourless, black).

Individual colour counts were saved and stored in a csv file for post-processing.

In an example organic product, an image frame of the reaction vial was recorded by the webcam, and the pixel count was extracted. Exemplary values are given in the table below. The solution colour corresponds to the highest count value, in this case red.

| Colour | Counts |
|---|---|
| Red | 58310 |
| Orange | 389 |
| Yellow | 270 |
| Blue | 546 |
| Colourless | 186 |
| Black | 1572 |

2.4 Stock Solutions

The stock solutions used in the organic reactions described above were:
o-Nitro-aniline: 0.01 M in acetone/1.7 M HCl, at 1:1
2-6-Dimethyl-aniline: 0.01 M in acetone/1.7 M HCl 1:1
Sodium 4-amino-5-hydroxy-2,7-napthalenedisulfonate hydrate: 0.01M in acetone/HCl 1.7 M 1:1
Sodium nitrate: 0.01 M in water
Sodium hydroxide: 0.5 M in water 2.5 Full Grid Scan The 117 reactions grid was fully explored with two platforms in 88 hours using a simple program.

The board started by adding the first aniline derivate and sodium nitrate in a reaction flask. After waiting 2 minutes for the diazonium salt synthesis it subsequently added the second aniline to the flask. After 30 minutes, the reaction was deemed complete, and the solution was diluted and then a base added.

During each reaction the board recorded four frames, as listed below:
"start": at reaction start, after addition and mixing of the reagents.
"finish": at reaction completion at 30 minutes.
"diluted": at dilution, 5 mL of the reaction solution (out of the 6 mL reaction mixture) is removed and replaced with water.
"base": after NaOH solution is added to the diluted mixture.

Image frames were analysed with the colour detection and plotted in order to visualize the colour distribution. Exemplary portions of the grid scan are shown in FIG. 4. Here, each plot shows a specific reaction moment. At bottom is the identity of the aniline derivative used first, and at left is the identity of the aniline derivative used second, with subplots showing the 13 different combination ratios used in the stud, with each plot showing the colour of the product.

2.6 Collaborative Algorithm

Two identical and physically separated platforms were used to explore the 117 reaction grid. Each platform ran the same algorithm with the aim of finding a blue reaction product mixture using a random search through the available reaction space, sharing experimental results in real time using Twitter to reduce total time.

The algorithm started by each system selecting a random reaction and sending a Tweet with the reaction parameters. The system then performed the selected reaction and saved the four frames as noted above. These frames were analyzed on board, the database was updated and an "end" Tweet with the results was sent. If a blue reaction was not present in the database, the board then restarted with a new random reaction, otherwise it would send a "stop" Tweet and the reaction process would be stopped.

A separated thread in the background checks every 5 minutes for Tweets from the other board and updates the database with the reaction results from the other system. In this way both boards avoided performing the same reaction twice.

FIG. 9 is a schematic flow diagram for the collaborative algorithm run by two identical and cooperating platforms.

This script was used to look for a blue reaction out of 117 total combinations. After 14 separate repeats of the space exploration, blue was found on average after 15.1 reactions (where the mathematical average of 3 blue reactions out of 117, shared on two platforms is calculated as 19.5).

3. Part II—Physical

To explore the real-time aspect of the networked synthesisers, a chemical oscillator based on the Belousov-Zhabotinsky reaction (BZ reaction) was investigated (see Epstein et al.), in which two physically separated oscillators have been synchronised in real time (see Makki et al.; Blagojevic et al.).

The reaction consisted of the oxidation of malonic acid by potassium bromate, catalysed by a metal-complex in acidic aqueous solution. Initially the synthesisers begin the reactions at different starting points and, through image analysis, data sharing and chemical adjustments, they used a synchronisation algorithm to reach identical oscillation periods. By ensuring constant stirring, the oscillations showed stable dynamics via the webcam, and the period was recorded and calculated on-board the robot with a real-time image analysis algorithm. Different strategies to achieve a control over the oscillation period have been reported in the literature, either by using the ratio of starting materials, the stirring speed or the temperature. Here the oscillation period was modulated in real time while the reaction was already running by using small additions of starting materials. To do this, potassium bromate, and water were selected respectively to increase and decrease the oscillation period through a series of controlled additions, where two functions were used to predict the behaviour of the reaction (see FIG. 5).

While one synthesiser acted as the 'Leader', simply sharing its period every 4 minutes, the other acted as a 'Follower', trying to synchronize its own period with the one of the Leader. Within a few iterations, and by applying the empirical functions, the two periods were successfully synchronized in real time with an uncertainty of 2 seconds. To explore this, the periods of both synthesisers were recorded for 90 minutes showing that the reactions kept oscillating at the same frequency.

To demonstrate the reliability of the platform the inventors managed to send a message between two oscillating systems by encoding it into a change in frequency. The message was split into individual characters and each was converted into a number using an optimized alphabet (see FIG. 5-$a$). The number was converted into octal numerical system (base-8 numbers), and the digits of obtained octal were expressed using the degree of modulation of the reaction frequency by using the threshold table (see FIG. 5-$b$).

The experiment started with two separate systems oscillating with different periods. When synchronization was achieved, the Leader added the reagent to change its frequency by the difference associated with the message, and then the Leader sends the amount of reagent added in this step to the Follower (see FIG. 5-$c$). The Follower adds this amount of regent to its reaction, and measures the value of the new frequency. The new frequency should be the same for both systems, and the difference is the encoded message.

In FIG. 6 the details of the encoded message for the partial word "cron" are shown as an example. However, the amount of material to obtain the period difference depends on the current period of the reaction and is calculated in real-time during the encoding/decoding.

Accordingly, the encoded message is not a direct translation, but depends on the Leader's reaction period and can be successfully decoded only if the Follower's reaction is oscillating at the same speed. Since a single experiment can hold up to four additions in a reliable way it is possible to send two characters for each BZ reaction before proceeding to the automatic clean cycle. In the present case, a program to perform a series of reactions and send a message of unlimited length was written and was used to successfully encode/decode "cronin lab".

3.1 Reaction Parameters and Recording

| Stock solutions: | Standard receipt: |
|---|---|
| 1M malonic acid in water | 1.67 mL of malonic acid solution |
| 0.5M potassium bromate in 1M sulfuric acid | 1.8 mL of potassium bromate solution |
| 1M sulfuric acid in water | 1.25 mL of sulfuric acid solution |
| $1 \times 10^{-3}$ M ferroin solution in water | 0.88 mL of ferroin solution |

The reaction consisted of the oxidation of malonic acid by bromate, catalysed by metal ions or metallo-complexes in acidic aqueous solution. The oscillations were visible as blue/red colour changes owing to the action of the ferroin, which acted both as catalyst and indicator in the reaction mixture.

During each experiment a webcam data stream was analyzed by the pcDuino in order to extract the oscillation period and make real time decisions.

The count of blue pixels was also saved in a .csv file on the board for post-processing.

Due to the limited computational power of the pcDuino for real time analysis the frame rate was set to 3 fps. This was considered acceptable since each BZ oscillation lasted for about 2-3 seconds.

FIG. 10 (top) shows the change in normalized pixel count over time for the blue and red counts. The change in averaged green count over time is also shown.

3.2 Plotting the Oscillation

In order to better observe the oscillation period behaviour over time, a script for data processing was created.

FIG. 10 (middle, bottom) shows the change in blue/red pixel ratio and the change in oscillation period over time.

3.3 Predicting the Chemical Influence on Oscillation Period

In order to predict the behaviour of the oscillation period when small amounts of water and potassium bromate are added we monitored several reactions while constant and regular additions were made. By processing the results, it has been possible to obtain two functions that correlate the amount of material added with the oscillation period change, within a reasonable time window and error.

$$\text{Shape of the curve is}: \text{period} = k * e^{amount}$$

$$\text{Reversed form}: \text{amount} = \ln\left(\frac{\text{goal period}}{k}\right)$$

It will give an estimate of water amount to add in order to reach a specific period. Since it is referred to the reaction start, for real-time additions the current period also needs to be considered:

$$\text{amount} = \ln\left(\frac{\text{goal period}}{k}\right) - \ln\left(\frac{\text{current period}}{k}\right)$$

It easy to see that the empirical constant k is irrelevant, the function used to predict water additions is:

$$\text{amount} = \ln(\text{goal period}) - \ln(\text{current period})$$

By using the data obtained in multiple addition tests the first empirical function was obtained $$\text{amount} = \frac{\textit{num} \text{ value}}{\text{current period}^2 - \text{goal period}^2}$$

Since the numerical value is not constant but depends on the period difference, a series of real additions at different periods have been used in order to obtain this correlation.

By replacing the numerical value with its dependence the final empirical function for bromate additions was obtained:

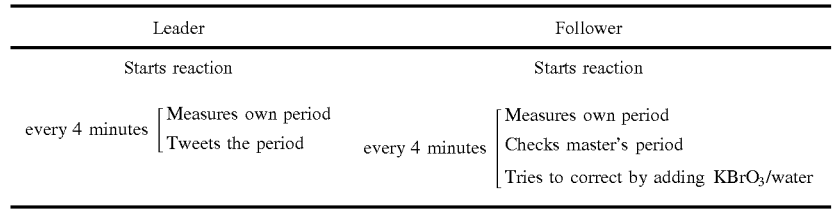

$$\text{amount} = \frac{6.2356(\text{current period} - \text{goal period})^{1.67}}{\text{current period}^2 - \text{goal period}^2}$$

FIG. 11 shows the change in blue/red pixel ratio and the change in oscillation period over time, with addition of water or addition of bromate to the reaction mixture.

3.5 Period Synchronization

By using real time additions of water and potassium bromate two BZ reaction were successfully synchronized in real time using Twitter. FIG. 12 shows the two boards starting with different oscillation periods: around 20 seconds the Leader (red line) and around 65 second the Follower (blue line). The process for the system to operate in leader-follower mode is shown below.

| Leader | | Follower |
| --- | --- | --- |
| Starts reaction | | Starts reaction |
| every 4 minutes ⎡ Measures own period ⎣ Tweets the period | every 4 minutes | ⎡ Measures own period ⎢ Checks master's period ⎣ Tries to correct by adding KBrO₃/water |

As soon as the reaction started to oscillate, the Leader board began to extract its own oscillation period through the webcam and Tweet this information every 4 minutes.

After 40 minutes the Follower started to monitor its own period in the same way and to check the Leader's period. By using the empirical functions, the algorithm made an estimation of the amount of starting material to add in order to synchronize its period with the Leader's one. Within a few iterations the two periods were synchronized with an uncertainty of 2 seconds. The period of both platforms were recorded for the next hour and half showing that the reactions keep oscillating at the same frequency.

3.6 Message Encoding

The experiment began with two separate systems oscillating with different periods. After 10 minutes the Follower synchronized its frequency with the Leader. When synchronization was achieved the Leader added the material to change its frequency by a determined "difference", then sent the amount to the Follower. The Follower added this amount and checked the new frequency. The new frequency should be the same for both systems and the difference obtained was the encoded message. It is important to highlight that the period difference was a static value that contained the encoded message while the information shared between the robots (the amount of material to add) was variable and depended on the current oscillation period.

Procedure for Message Encoding

The message was split into individual characters and each was converted into a number using an optimized alphabet, from 0 to 63.

The number was converted into octal numerical system (base-8 numbers), the obtained octal was expressed using the degree of modulation of the reaction frequency. To represent an octal base there were 8 thresholds for oscillation period: 21, 15, 9, 3, −3, −9, −15, −21 seconds.

A single experiment could hold 4 additions, each corresponding to one octal number, in a reliable way. This means that it was possible to send two characters for each BZ reaction before needing to clean the reaction vessel and start a new one. A program to perform a series of reactions and send a message of any length was made.

4. Part III—Inorganic

To collaboratively search a chemical space for the purposes of evaluating reproducibility in the system of the invention (see Baker et al.), a complex cluster based upon a known tungsten polyoxometallate cluster was chosen as an illustrative target (see Symes et al.). Several reaction series of varying W/Se:Mn ratios were performed collaboratively by two platforms communicating in real-time over Twitter.

In a first step, the inventors set out to establish the values of reagent stoichiometry and pH that would produce crystals of the target compound within 2 hours, as monitored by a webcam. The reaction conditions meeting this criterion were repeated to determine the reproducibility of the process. Full automation of the synthesis, reaction recording, and crystal recognition was achieved using the platform described above, combined with image analysis machine learning software.

A grid of 120 reactions was split into 8 series of 15 reactions, each of which was explored collaboratively between two platforms. To start each series, the Leader selects at random a reaction from the list of 15 shared between it and the Follower, and informs the reporting platform. The Follower repeats this step with the remaining 14 available reaction options and the process continues until the series has been completed. In real-time the network was informed with feedback about each reaction result i.e. observing precipitation or the formation of crystals or not. Reagents were added to the reaction vial in sequence and the resulting solution was stirred for 10 minutes. Following transfer of the reaction solution to a recording vial, suspended over a webcam, the reaction was recorded for 2 hours.

A machine learning crystal recognition method was developed by training a model from previous reactions and deployed during the 2 hour recording period. Many clear and crystalized reaction images from previous experiments were compiled into a database to train this model. The grid of 120 reactions was completed three times between the two collaborating platforms revealing 13 conditions in the space that produced crystals at least once. Each of these reaction conditions was repeated until a consistent average percentage of reproducibility emerged. If the reaction reached 15 failed experiments in a row it was abandoned as a stochastic anomaly. Of the 13 reaction conditions to have produced crystals at least once, 7 reactions never again produced crystals. The remaining 6 reaction conditions showed percentages of reproducibility of between 11.8-50%, with the optimum reaction conditions being a Mn:W ratio of 1:6 using 1.49 mL of 2.32 M HCl (see FIG. 6).

Peristaltic pumps supplied volumes of stock solutions to a reaction vial. Following 10 minutes of stirring at room temperature, the reaction solutions were transferred to recording vials, suspended over a webcam, again using a peristaltic pump. Reactions are recorded and analysed in real-time for crystal formation and results are stored on a local network. Once complete both reaction and recording vials are extensively cleaned with an automated cycle for the process to begin again.

Image analysis techniques were developed to allow for full automation of reaction monitoring. A large database of images was gathered for both clear and crystalized reaction solutions in order to train a model used for crystal recognition in real-time via a HD webcam. A frame of the reaction solution was taken every 8 seconds and analysed for the presence of crystals using this model. Once a specific threshold of frames containing crystals was met, the program determined the reaction a success and updated the network. If no crystals were observed after 2 hours, the platform started a cleaning cycle and continued with the remaining reactions.

Further image processing of the early reaction solutions using colour analysis (Hue) was deployed to identify precipitated reactions. Precipitation occurs most often within the first few minutes of the reaction recording. After 5 minutes of reaction recording a frame was analysed using this method. A mask was applied to isolate the reaction solution, a colour conversion from RBG to HSV (Hue, Saturation, Value) was applied, and largest representative Hue value was returned. A Hue value above 160 in all cases was seen for all precipitates. This method was found to be highly reliable and saved a great deal of time running the platform long term. Simple python commands were used to preform and report on the reactions to a network.

4.1 Synthesis

Stock solutions used:

$Na_2WO_4.2H_2O$ (75 g), $Na_2SeO_3$ (6 g), DMA.HCl (30 g) in 450 mL $MnCl_2.4H_2O$ (9.36 g) in 450 mL 2.32 M HCl (57.1 mL of concentrated acid made to 300 mL)

The stock solutions were aqueous stock solutions.

The polyoxometallate chosen for this study was previously reported by the inventor and his group. Formula: $[W_{19}M_2O_{61}Cl(SeO_3)_2(H_2O)_2]^{9-}$ (see *Nature Chemistry* 4, 349-354 (2012).

4.2 Stage One—Collaboratively Explore a Chemical Space

At each stage of synthesis and analysis both platforms update shared network files for the other to read and proceed accordingly. For example, when one platform selects a reaction volume at random to explore, the other will acknowledge it and remove it from its own series before continuing with its own choice. Conditions that have produced crystals are stored by both platforms for repetition later.

FIG. 13 has a flow diagram showing the processes in the first stage.

4.3 Stage Two—Repetition of Successful Conditions

The successful reactions conditions from the collaborative stage were compiled and repeated in order to establish the reproducibility of the chemistry/crystallization. One set of conditions was chosen and both platforms performed repeat reactions. Once enough data had been collected to establish an average percentage reproducibility under one series of reaction conditions, the next set of reaction conditions was investigated.

FIG. 13 has a flow diagram showing the processes in the second stage.

4.4 Reproducibility of Crystallization

The stochastic nature of synthesis and crystallization in inorganic chemistry is a significant contributing factor to the growing crisis of reproducibility. The crystallizing conditions found during the collaborative chemical space search were repeated on both platforms as many times as were needed to quantify the percentage of reproducibility of these two processes.

For the example described above, two of the five crystallizing conditions using 1.43 and 1.53 mL of acid never again produced crystals during repeat experiments. However acid volumes 1.48, 1.49 and 1.50 mL revealed reproducibility of between 37.5-50%.

4.5 Grid Search of Reaction Conditions

Multiple 8 reaction series, each with varying Mn:W ratios, were performed collaboratively by the methods detailed above using two synthesisers. Each reaction series varied in acid volume from 1.4-1.54 mL HCl (approximately between pH 3-6.5) and each reaction was monitored by web cam for crystal formation within 2 hours of reaction completion. The full grid was repeated 3 times to more thoroughly explore the space. The results of each grid can be seen in FIG. 6 as 2D colour maps.

Each of the conditions marked in red in FIG. 6 produced crystals at least once during these automated runs. All these reactions were subsequently repeated to assess the likelihood of growing crystals again. After 15 repeat reactions, if no crystals had been produced, the reaction was abandoned and the next set of reaction conditions was used.

A significant number of these crystalizing conditions never again produced crystals. Others varied from 10-50% in frequency of crystal formation across up to 48 reactions. Shown in FIG. 14 is a 3D representation of the likelihood of crystal formation for all conditions of the chemical space, and the top 6 conditions for crystal formation without 2 hours are set out in the Table below.

TABLE 1

Reproducibility of Most Reproducible Reaction Conditions

| Mn:W Ratio | Total volume mL | Acid volume mL | Reproducibility % |
|---|---|---|---|
| 1:6 | 10.38 | 1.49 | 50 |
| 1:6 | 10.37 | 1.48 | 41.7 |
| 1:6 | 10.39 | 1.5 | 37.5 |
| 1:8 | 9.35 | 1.46 | 20.6 |
| 1:6 | 10.4 | 1.51 | 15 |
| 1:8 | 9.34 | 1.45 | 11.8 |

5. Agent Based Simulation

Figure 1:
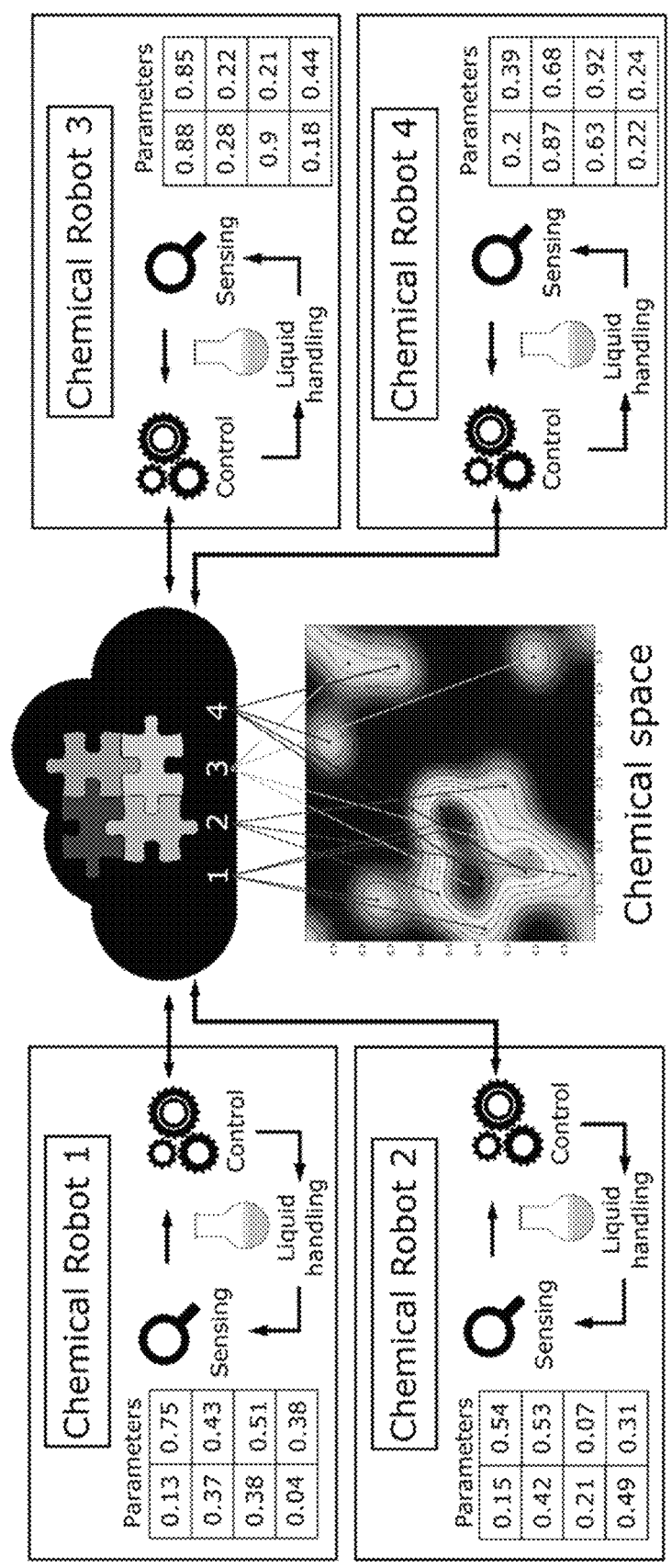
FIG. 1 is a schematic of a system according to an embodiment of the invention. Here four physically separated synthesiser units (ChemPUs) are connected to a cloud via the internet.

To demonstrate the importance of information sharing between synthesisers, computer simulations of the relevant strategies were developed (see FIG. 1). Each simulated synthesiser performed experiments randomly until the target experiment was conducted.

The simulations were performed over three different approaches. The random strategy was the most basic, where the synthesisers have no memory of the reactions they have conducted previously. As an example, where the reaction space has 10 locations, the synthesiser might randomly decide to look at location number 7 first, if the goal isn't there than it will choose another location to search. When making the decision this second time the synthesiser does not remember that it had tried location 7 already without success and so is as likely to pick that location again as any other The second strategy is called the individual strategy. In this case the synthesisers remember their past. Thus for the example case above, after trying location 7 the synthesiser would not check it again. However, using this strategy one synthesiser still acts independently from other synthesiser, as there is no information sharing between the synthesisers.

The final strategy is collaborative. Each synthesiser knows its own actions and those of all other synthesisers. It is this pooling of information that makes the collaborative strategy the most favourable. FIG. 1a shows the search efficiency as the percentage of the possible space that was searched before the goal was reached.

For all cases the average number of experiments that needed to be performed is the highest for the random strategy, better for the individual strategy and lowest for the collaborative. In the case of a single synthesiser, the collaborative strategy reduces to the individual. From that point, as the number of robots increases, the advantage of the collaborative strategy becomes more pronounced as the individual strategy becomes less advantageous. The individual strategy is useful with a small number of synthesisers but has diminishing returns with increasing numbers of agents. An increase of one synthesiser from one to two yields a 50% improvement while an increase from two synthesisers to three yields a lower improvement of 33.3% and so on.

The simulations show that the collaboration strategy is by far the most efficient and that as the number of available synthesisers increases the benefit of using collaboration increases as well.

FIG. 1b shows that for all strategies, the total number of searches that had to be conducted decreases. With the y-axis logarithmic, the constant slopes show that the improvement in searching is exponential. The individual strategy will always be better than the random one, no matter the number of agents, yet by a narrowing margin. As expected all strategies improve with an increase in the number of synthesisers yet the collaborative strategy is superior to both the random and individual strategy under any conditions.

6. Game

Two synthesisers were permitted to compete over a game of Hex, using the results of a chemical process to determine the board moves. Both synthesisers began the game series with identical reaction spaces to explore, in search of new chemical discoveries determined by colour. The chosen reaction space consisted of the same three aniline derivatives described in FIG. 3. The game logic was based on the rarity of the reaction result; if a new/rare colour was found, the optimal move was allowed. However if the result has been seen many times, a sub-optimal or random move was allowed on the game board. Once the winner of the first game emerged, a new strategy was applied to the losing platform. In this case the reaction space (possible combinations of same three aniline compounds) was increased for the loser, in the hope of finding new results (see FIG. 7). The platforms communicated via a shared server that updated the live game board and optimal movements are determined by a Hex game algorithm using Monte-Carlo simulations.

A typical game sequence can see between two to five games completed between two players before the reaction space is complete. FIG. 8 shows a typical sequence of 4 complete games ($5^{th}$ remained incomplete) in which the losing strategy, over time, produces significantly more unique discoveries then a continued search of the original reaction space.

6.1 General Overview

Two automated platforms were tasked with playing a game of Hex. New/rare reaction results allowed the player to use the optimum movement (determined algorithmically described later) with uncommon/common results allowing only for sub-optimal/random movements. Losing games trigger a change in strategy for the losing platform, in this case an expansion of the reaction grid the player was allowed to explore. The idea was to show that a game outcome could drive a player to either change or maintain its current strategy in the hope of making more chemical discoveries in future. The chemistry chosen for this project was the same seen in the Organic section above, and the results were gathered and analyzed via web-cam.

6.2 Decision Making

The goal for players in a Hex game is to connect one side of the board with the opposite side using a continuous line of that player's color. The game cannot end in a draw. From a randomly assigned first board position or the current state of the board, the optimal movement was calculated using Monte-Carlo simulations with the goal of completing the game. Once an optimal movement has been calculated, the results of the chemistry determine if the player may use it. Colour rarity vs move selection allowance is determined by the following:

| | |
|---|---|
| Unique/Rare colors observed up to 4 times | Optimal movement |
| Uncommon Colors observed between 5 and 7 times | Sub-optimal movement |
| Common Colors observed more than 7 times | Random movement |

Sub-optimal movements were defined as a position beside, above or below the optimal and was selected based on availability.

6.3 Communication Between Platforms

In order to keep both players in sync with one another, a remote server was developed to handle all communications between the platforms. Each platform selected a reaction and processed the information through image analysis and the decision-making algorithm as described previously. The selected move was then sent to the remote server from the platform for processing. All logic for the game, such as updating board movements, was handled by the server. Once an iteration of the game was completed, the server broadcasted a message to all connected clients detailing who had won the game. The players then adjusted their strategies accordingly.

The reasoning behind developing a remote server system for this task was a separation of concerns. By separating the game logic from the platforms, as opposed to each platform having its own representation of the game, the risk of each platform falling out of sync with one another was minimized, thereby preventing inaccurate results. Potential race conditions with platforms attempting to access a single file at the same time were also prevented. A single server with file access eliminated this risk. The design of the server allows for multiple concurrent connections and data processing which opened the possibility of increasing the number networked platforms working towards a common goal.

6.4 Strategy

Both players begin the first game in the sequence by selecting reactions from an identical chemical space (see FIG. 15 (middle)). Once the loser of the first game was established, that player was allowed to access a new strategy/expanded grid (FIG. 15, right), whilst the winner continues with the original. Each strategy/chemical space consisted of 9 grids small grids of two aniline derivatives labelled A, B and C (FIG. 15, left). The change of the reaction space from the original to the expanded was achieved by adding two extra values of reagent volume to each of these 9 smaller grids. The stock solutions and experimental protocol are identical to those described in the Organic section above.

Given that the game sequence proceeds one platform after another, the original reaction space restricts the total reaction number to 81 for each player (9 grids of 3×3 reagent volumes). A typical game sequence could consist of between 2-5 completed games. Shown in FIG. 8 is a game sequence with 4 complete games in sequence ($5^{th}$ game was incomplete) in which the losing strategy was adopted by player 2 after game 1. Against the logical expectation the losing strategy, whilst allowing player 2 to win game 2, did not result in many new unique discoveries. However, when player 1 adopted the losing strategy after game 2, its unique discovery count increased significantly, but did not result in a victory for the remained of the total game sequence. This can be explained simply by the fact a game is still based on probability and a new advantageous strategy will work most, but not all of the time.

REFERENCES

All documents mentioned in this specification are incorporated herein by reference in their entirety.

Baker, M. & Penny, D. Nature 533, 452-454 (2016).
Blagojević, S. M., et al. Phys. Chem. Chem. Phys. 10, 6658 (2008).
Epstein, I. R. & Showalter, K. J. Phys. Chem. 100, 13132-13147 (1996).
GB 2372506
Gung, B. W. & Taylor, R. T. J. Chem. Educ., 81, 1630-1632 (2004).
Ingham, R. J. et al. Angew. Chemie—Int. Ed. 54, 144-148 (2015).
Kitson, P. J., Glatzel, S., Cronin, L. Beilstein J. Org. Chem., 12, 2776-2783 (2016).
Li, J., et al., Science 347, 1221-1226 (2015)
Machida, K., et al. Chem Pharm Bull. 58, 87-93 (2010).
Makki, R., Muuzuri, A. P. & Perez-Mercader, J. Chem.—A Eur. J. 20, 14213-14217 (2014).
Perkel, J. M. Nature, 542, 125-126 (2017).
Prabhu, G. R. D. & Urban, P. L. Trends Anal. Chem. 88, 41-52 (2017).
Pronk, S. et al. Bioinformatics, 29, 845-854 (2013).
Schrope, M. Proc. Natl. Acad. Sci. 110, 7104-7106 (2013)
Skilton, R. A. et al. Nat. Chem. 7, 1-5 (2015)
Sørensen, J. J. W. H. et al. Nature, 532, 210-213 (2016).
Symes, M. D. et al. Nat. Chem. 4, 349-354 (2012).
US 2003/012700
US 2008/0286174
US 2016/0288081
US 2018/0010058
WO 2013/175240

The invention claimed is:

1. A system comprising a plurality of synthesisers that are in communication via a communal reporting platform, wherein each synthesiser is programmed for the automated synthesis of one or more chemical or biological reactions, and each synthesiser comprises a reaction vessel which is supplied by a reagent delivery system, an analytical system for analysing a reaction, and a controller for managing the reagent delivery system and the analytical system, and for communication with the reporting platform, wherein each controller is configured for:
    posting information to the reporting platform;
    observing the posted information on the reporting platform; and
    selecting a future reaction for performance in the corresponding synthesizer, based on the posted information on the reporting platform.

2. The system according to claim 1, wherein the reporting platform is a remotely-located server or a cloud-based system.

3. The system according to claim 1, wherein the reporting platform is a social media platform.

4. The system according to claim 1, wherein the reporting platform publicly displays reaction information received from the synthesisers.

5. The system according to claim 1, wherein the reporting platform is adapted to display reaction information in the form of imagery and/or text string.

6. The system according to claim 5, wherein the analytical system is provided with a camera for recording still or video images, for communication to the reporting platform.

7. The system according to claim 5, wherein analytical data recorded by the analytical system is translated to a text description of the reaction, which text description is provided to the reporting platform for posting as a text string.

8. The system according to claim 1, wherein the synthesisers are remotely located from each other and from the reporting platform.

9. The system according to claim 1, wherein the plurality of synthesisers comprises a first synthesiser and a second synthesiser, and wherein the first synthesiser in the system has priority status over the second synthesiser in the system.

10. The system according to claim 1, wherein the system is adapted to receive a further synthesiser into the system, and the system is adapted to disconnect a synthesiser of the plurality of synthesisers from the system.

11. The system according to claim 1 which is a secure system, such that only controllers of synthesizers of the plurality of synthesisers in the system that have approved status can communicate with the reporting platform, post information to the reporting platform and access information posted to the reporting platform by other controllers of synthesisers of the plurality of synthesisers in the system.

12. The system according to claim 1, wherein a synthesiser of the plurality of synthesisers is programmed with an algorithm to select reactions for performance based on an analysis of communal reaction information held by the reporting platform.

13. The system according to claim 5, wherein the analytical system is provided with a camera for recording colour still or colour video images, for communication to the reporting platform.

14. The system according to claim 1, wherein a synthesiser of the plurality of synthesisers is programmed with a genetic algorithm to select reactions for performance based on an analysis of communal reaction information held by the reporting platform.

15. A method of performing a plurality of reactions, the method comprising the steps of:
  (i) providing a system according to claim 1, where the system comprises a plurality of synthesisers, wherein each synthesiser is in communication via a communal reporting platform;
  (ii) permitting each controller of each synthesiser to select an intended reaction for performance, and allowing each controller of each synthesiser to post its intended reaction to the reporting platform;
  (iii) allowing each synthesiser to perform its intended reaction and each controller to post a reaction result to the reporting platform;
  (iv) allowing each controller of each synthesiser to observe the posted reaction results on the reporting platform; and
  (v) permitting each controller of each synthesiser to select an intended future reaction for performance based on the posted reaction results, where that intended future reaction optionally differs from the reactions previously reported by the controllers of all synthesisers to the reporting platform.

16. The method according to claim 15, wherein in step (v) the intended future reaction differs from the reactions previously reported by the controllers of all synthesizers to the reporting platform.

17. The method according to claim 15 or claim 16, wherein each synthesiser performs reactions that are not performed by any other synthesiser in the system.

18. The method according to claim 15, wherein the plurality of synthesisers comprises a first synthesiser and a second synthesiser, and wherein the first synthesiser has priority status over the second synthesiser, and the first synthesiser is permitted to perform an intended reaction in preference over the second synthesiser.

19. The method according to claim 15, wherein in a preliminary step each controller of each synthesiser indicates to the reporting platform which chemical and physical inputs are available for use with its synthesiser.

* * * * *